(12) United States Patent  (10) Patent No.: US 6,551,117 B2
Poplawski et al.  (45) Date of Patent: *Apr. 22, 2003

(54) REMOVABLE TRANSCEIVER MODULE

(75) Inventors: Daniel S. Poplawski, Montgomery, IL (US); Patrick B. Gilliland, Chicago, IL (US); James W. McGinley, Barrington Hills, IL (US)

(73) Assignee: Stratos Lightwave, Inc., Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/920,421

(22) Filed: Aug. 1, 2001

(65) Prior Publication Data

US 2002/0009905 A1 Jan. 24, 2002

Related U.S. Application Data

(63) Continuation of application No. 09/295,743, filed on Apr. 20, 1999, now Pat. No. 6,267,606, which is a continuation of application No. 09/097,210, filed on Jun. 12, 1998, now Pat. No. 6,220,878, which is a continuation of application No. 08/538,897, filed on Oct. 4, 1995, now Pat. No. 5,864,468, which is a continuation of application No. 08/515,813, filed on Aug. 16, 1995, which is a continuation-in-part of application No. 08/485,310, filed on Jun. 7, 1995, now Pat. No. 5,734,558, which is a continuation-in-part of application No. 08/417,914, filed on Apr. 6, 1995, now Pat. No. 5,717,533, which is a continuation-in-part of application No. 08/372,780, filed on Jan. 13, 1995, now Pat. No. 5,546,281.

(51) Int. Cl.[7] .......................................... H01R 13/648
(52) U.S. Cl. ........................ 439/92; 439/607; 439/350; 439/357; 439/65; 439/74; 361/752
(58) Field of Search ............................ 439/92, 95, 105, 439/108, 607, 74, 65, 350, 357, 358; 365/92; 361/752, 753, 756, 802

(56) References Cited

U.S. PATENT DOCUMENTS

| | | | | |
|---|---|---|---|---|
| 4,756,593 A | * | 7/1988 | Koakutsu et al. | 385/139 |
| 4,912,521 A | * | 3/1990 | Almquist et al. | 359/152 |
| 4,969,924 A | * | 11/1990 | Suverison et al. | 385/78 |
| 5,202,943 A | * | 4/1993 | Carden et al. | 385/92 |
| 5,353,364 A | * | 10/1994 | Kurashima | 257/433 |
| 5,534,662 A | * | 7/1996 | Peacock et al. | 174/35 GC |
| 5,546,281 A | * | 8/1996 | Poplawski et al. | 361/752 |
| 5,734,558 A | * | 3/1998 | Poplawski et al. | 361/752 |
| 5,864,468 A | * | 1/1999 | Poplawski et al. | 361/752 |
| 5,879,173 A | * | 3/1999 | Poplawsi et al. | 385/92 |
| 6,220,878 B1 | * | 4/2001 | Poplawski et al. | 439/92 |
| 6,267,606 B1 | * | 7/2002 | Poplawski et al. | 361/752 |

* cited by examiner

*Primary Examiner*—Tho D. Ta
*Assistant Examiner*—Edwin A. León
(74) *Attorney, Agent, or Firm*—Steven M. Evans

(57) ABSTRACT

A robust optoelectronic transceiver module which is quick, easy, and inexpensive to manufacture. The transceiver module has a main housing which consists of a circuit board having an optical subassembly mounted thereon. The module housing may be pluggable via a retention member received within the receptacle. The module and receptacle assembly may include grounding member such as a ground clip mounted within a gap provided between the module and a connector port of the receptacle to limit electromagnetic emissions.

41 Claims, 9 Drawing Sheets

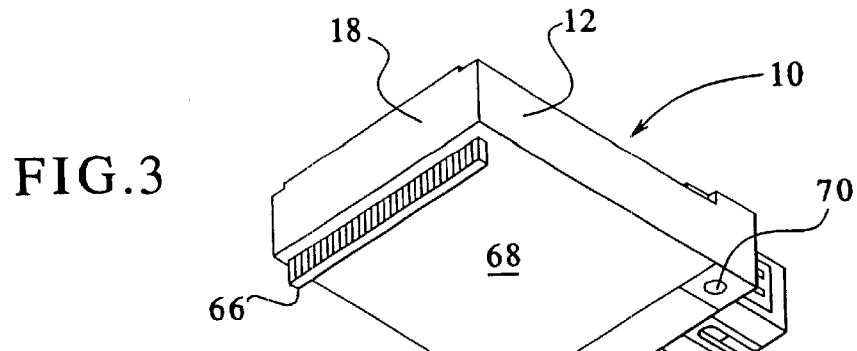
FIG.3
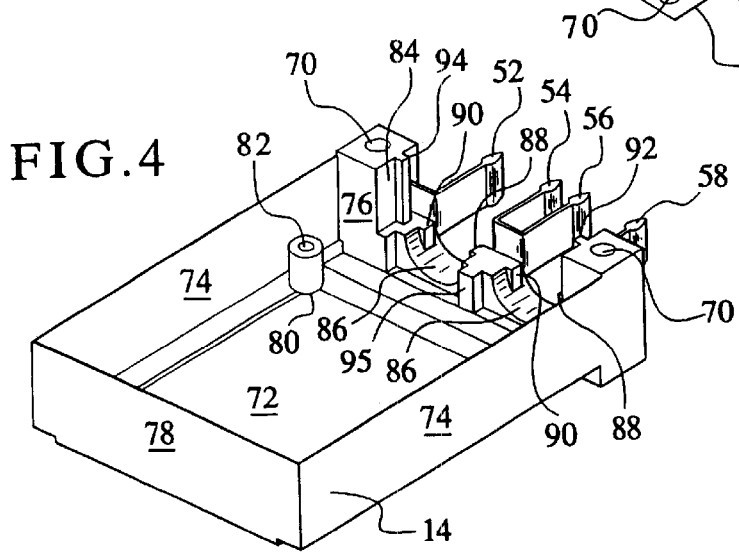
FIG.4
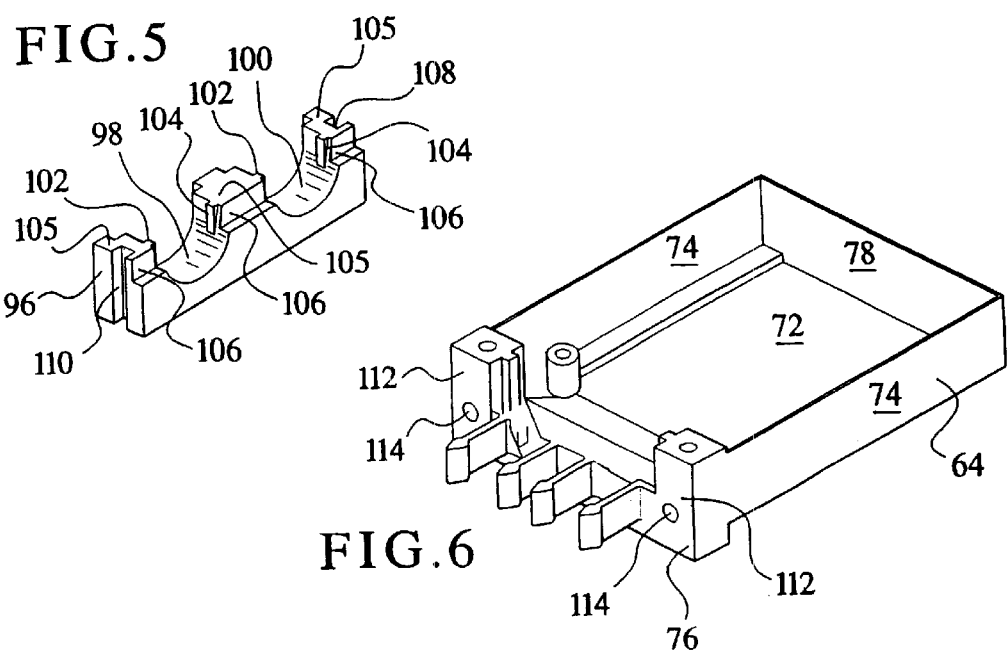
FIG.5
FIG.6

REMOVABLE TRANSCEIVER MODULE

This is a continuation of application Ser. No. 09/295,743 filed Apr. 20, 1999 now U.S. Pat. No. 6,267,606 which is a continuation of U.S. Ser. No. 09/097,210 filed Jun. 12, 1998 now U.S. Pat. No. 6,220,878 which is a continuation of U.S. Ser. No. 08/538,897 filed on Oct. 4, 1995, U.S. Pat. No. 5,864,468 and Ser. No. 08/515,813 filed on Aug. 16, 1995 which is a continuation-in-part of U.S. Ser. No. 08/485,310, filed on Jun. 7, 1995, U.S. Pat. No. 5,734,558 which are both continuations-in-part of U.S. Ser. No. 08/417,914, filed on Apr. 6, 1995, U.S. Pat. No. 5,717,533 and U.S. Ser. No. 08/372,780, filed on Jan. 13, 1995, U.S. Pat. No. 5,546,281.

BACKGROUND OF THE INVENTION

This invention relates generally to optoelectronic transceiver modules and in particular, it relates to an optoelectronic transceiver module, and its method of manufacture, whereby the module is inexpensive to manufacture, has a small yet robust package, and can be installed and replaced via a ribbon style connector for interchangeability and easy removal, provides for static discharge, and can be installed and replaced via a ribbon style connector.

Optoelectronic transceiver modules provide for the bi-directional transmission of data between an electrical interface and an optical data link. The module receives electrically encoded data signals which are converted into optical signals and transmitted over the optical data link. Likewise, the module receives optically encoded data signals which are converted into electrical signals and transmitted onto the electrical interface.

Normally, the transceiver is mounted onto one of the circuit card assemblies of a host computer, input/output system, peripheral device, or switch. Therefore, as with all electronic equipment, there is a need for a transceiver having an outer package design which occupies as little circuit card surface area as possible.

In addition, there is a need for a transceiver module which is highly reliable and durable. One method presently used to ensure reliability and durability is to encapsulate the electronics of the transceiver within an insulative potting material. Encapsulating the transceiver electronics results in reducing vibration sensitivity and prevents unauthorized personnel from meddling with the module's electronics.

Presently, the molding of the potting material around the transceiver electronics is performed by placing the electronics within a silicone mold. Any portion of the electronics which extends outside of the mold is caulked, by hand, with a silicone compound which provides for a liquid tight seal. Once the mold is sealed, potting material is inserted therein. After the potting material is allowed to cure, the silicone mold is peeled away from the newly formed module.

The above described prior art molding process has several drawbacks. For example, it is time consuming and results in a transceiver module which has a pitted outer surface. In addition, the silicone mold used in the molding process has a limited life of only three to five modules before a new mold must be employed.

The optoelectronic module is provided with a plurality of electrical pins for forming an electrical connection with a circuit card assembly. The electrical pins consist of solid wire strands with each pin having one end connected to the electronics within the module and the other end protruding from the module's potting material.

The portion of each pin which protrudes from the potting material is either soldered within a plated through-hole, which is provided by the circuit card assembly, or placed within a connector which grasps onto the pin. However, the flimsy wire pins are very susceptible to deformation during both the normal handling of the module and its removal and installation onto a circuit card assembly. Thus, the flimsy pins currently used in the prior art are difficult and time consuming to attach to a circuit card assembly since they must be periodically inspected and realigned. Furthermore, the pins may break if they are realigned too many times.

In addition to the electrical pins, the module also is equipped with two mounting ports for physically securing the module onto the circuit card assembly. The module is placed onto the circuit card assembly so that the mounting ports align with holes provided in the circuit card assembly. Once the module is properly aligned, screws are inserted through the holes in the circuit card assembly and into the mounting ports of the module. The screws are then tightened until the module is firmly affixed to the circuit card assembly.

Similarly, to remove the module from the circuit card assembly, the screws must be removed and the wires either unsoldered from the circuit card or pulled from the connector which is a timely and expensive process requiring multiple components. In fact, it is common for the entire circuit card assembly to be changed in order to change the transceiver module or the media interface.

Finally, once the module is secured to the circuit card assembly, optical fibers contained within an SC duplex plug connector are mated to the module. Normally, the SC duplex connector has a plastic housing which may be statically charged. Thus, its connection onto the transceiver module may result in damage to the electronic components within the module unless proper grounding of the SC connector is provided.

It should be appreciated by those skilled in the art that the possibility of damage due to static discharge is not only applicable to transceiver modules which mate with an SC duplex connector. Other optoelectronic modules, such as, for example, Gigabaud Link Modules (GLM), are also susceptible to static discharge damage whenever they are mated to a connector containing optical fibers.

Therefore, there is a need for a transceiver module which provides for a small, yet robust package, which is inexpensive to manufacture and can easily and quickly be installed and removed from a circuit card assembly in the field provides for static discharge, and can easily and quickly be installed and removed from a circuit card assembly. The present invention is such an apparatus.

Likewise, there is a need for preventing a statically charged fiber optic connector from damaging the electronics within an optoelectronic module.

In view of the above, it is an object of the present invention to provide a small transceiver module package.

It is another object of the present invention to provide a module package that has a robust and tamper resistent design.

Also, it is an object of the present invention to provide a module which can quickly be installed and removed from a circuit card assembly.

Another object of the present invention is to provide a module package design that can quickly and easily be produced.

A further object of the present invention is to provide a module package that can be produced inexpensively.

It is yet another object of the present invention to prevent a statically charged connector from damaging the electrical circuitry within an optoelectronic module by pregrounding the plug connector.

Furthermore, it is an object of the present invention to provide a module with a coating which dissipates an electrostatic discharge and serves as an electromagnetic shield.

As well, it is an object of the present invention to provide a module which is easily and quickly pluggable and removed to and from a housing.

Another object of the present invention is to provide a receptacle to receive the module having a grounding means.

It is also an object of the present invention to provide a receptacle having a means for preventing the escape of electromagnetic radiation from the receptacle.

Furthermore, it is an object of the present invention to provide an interchangeable transceiver module to provide electrical or fiber optic connection.

SUMMARY OF THE INVENTION

In one form of the invention, a robust optoelectronic transceiver module is provided which is quick, easy, and inexpensive to manufacture. The transceiver module has a main housing which consists of a potting box with potting material inserted therein. In addition, a circuit board is encased by the potting material.

The invention further provides for an optical subassembly to be mounted on a circuit board. In addition, the potting box has a recess which allows the optical subassembly to extend outside of the potting box. Furthermore, a recess cover may be provided for forming a liquid tight seal between the recess cover, the potting box, and the optical subassembly.

The optoelectronic transceiver module may also have a ribbon style connector attached to the circuit board and protruding from the main housing. The ribbon style connector may protrude from either the bottom or one end of the main housing. In addition, the ribbon style connector may comprise of either a male ribbon style connector or a resilient male ribbon style connector.

In another form of the invention, an optoelectronic transceiver module is provided which mounts onto a circuit card assembly. The module has a main housing with a bottom. Protruding from the bottom of the main housing is a ribbon style connector which allows for quickly installing and replacing the module from the circuit card assembly.

In yet another form of the invention, a method of assembling an optoelectronic transceiver module is provided. The steps of the method consists of placing a circuit board within a potting box and injecting potting material within the potting box. In addition, the circuit board may be affixed within the potting box after the circuit board is positioned within the potting box. Furthermore, a liquid tight recess cover may be mounted within the potting box's recess after the circuit board is positioned within the potting box.

Also, the method of manufacture provides for coating the potting box with a conductive metal before the circuit board is placed within the potting box or after the potting material is injected within the potting box. Moreover, a connector shell may be mounted onto the potting box after the potting material is injected within the potting box.

In still another form of the invention, a method of assembling an optoelectronic transceiver is provided which includes the steps of affixing a circuit board within a housing and securing a conductive metal coating onto the housing.

In another form of the invention, a potting box is provided for potting optoelectronic components which include an optical subassembly. The potting box includes a wall having a recess which allows the optical subassembly to extend outside of the potting box. In addition, a recess cover is provided for forming a liquid tight seal between the recess cover, the potting box, and the optical subassembly. Furthermore, the invention provides for the potting box to have a standoff column for mounting a circuit board within the potting box and an alignment guide for engaging a groove within the recess cover.

In still another form of the invention, a housing is provided including release levers having detentes which mate with an aperture of a receiving receptacle. The release lever includes a first end integrally molded to the housing and a second distal end protruding outward away from the housing having a gripping portion and intermediate the first end and the second end and intermediate portion having a detente protruding perpendicular from the surface of the intermediate section. The housing of the transceiver includes a first end and a second end. At the first end of the housing is a transceiver connector for receiving fiber optic plugs. At the second end of the housing is a pluggable connector.

In another form of the invention, a transceiver module and receptacle assembly is provided comprising a transceiver module housing having a first end and second end, a latching means attached adjacent the first end, a pluggable connector at the second end and a grounding means associated with the receptacle. A receptacle housing is provided defining a chamber and the grounding means of the receptacle includes a ground tab protruding within the chamber. The ground tab is attached to an arm which is molded within the receptacle housing. The receptacle housing has a first end having a protective door mounted thereto. The door is hinged adjacent the top surface of the receptacle housing. The transceiver module housing includes a metallized grounding portion to come in contact with the grounding means of the transceiver receptacle in order to provide grounding of the transceiver module to the receptacle. The transceiver module external surface is metallized and upon insertion within the receptacle, the metallized transceiver module housing abuts against a ground tab protruding within the receptacle chamber in order to ground the transceiver module to the receptacle. The latching means includes release levers attached to the sides of the transceiver module housing and latching to the interior surface of the receptacle. A transceiver connector is attached to the first end of the transceiver module housing. The transceiver connector includes a fiber optic or electrical plug receptacle. The transceiver module includes an optoelectronic subassembly for an optical media interface or electronic subassembly for an electrical media interface.

In still another form of the invention a transceiver module receptacle is provided comprising a receptacle housing having a first end and a second end, a module receiving opening at the first end and an electrical connector at the second end. The first end includes a door hingedly attached at the first end. The door includes posts projecting from the edges for mounting the door to the housing. Spring means are mounted to the posts of the door. The receptacle housing includes an inner chamber having walls defining the chamber. A ground surface protrudes from the walls for contacting the grounding means of a transceiver module. The grounding surface is molded into the walls of the housing. The ground surface includes posts protruding through a bottom surface of the receptacle housing for mounting the receptacle to a motherboard.

In another form of the invention a transceiver module is provided comprising a transceiver module housing having a first end and a second end, a latching means attached adjacent the first end and a pluggable connector at the second end. The transceiver module includes a transceiver connector at the first end. The transceiver connector includes a modular port for receiving various media transducers. The media transducer includes a fiber optic plug receptacle and an optoelectronic subassembly or the media transducer includes an electrical plug receptacle and an electrical subassembly. The pluggable connector includes a D-shaped shroud surrounding a circuit board protruding transversely from the second end and having electrical contacts attached thereto. The pluggable connector includes ground contacts offset from adjacent electrical contacts.

In yet another form of the invention, an optoelectronic module is provided for mounting within a grounded structure, such as a computer chassis. The optoelectronic module consists of electrically conductive latches which are conductively connected to a structure which provides for the forming of an electrical connection with the grounded structure. The optoelectronic transceiver module may further include a transceiver connector attached thereto and which is conductively connected to the latches. Furthermore, a grounding clip may be attached to the transceiver connector. The grounding clip may have at least one tab extending therefrom. Accordingly, the optoelectronic module may use at least one tab for conductively connecting the latches to the grounded structure.

In a further form of the invention, a removable optoelectronic transceiver module and receptacle assembly is provided comprising a transceiver module housing having a first end, a second end and an electrically conductive outside surface, a circuit board mounted within the housing and an optical subassembly electrically connected to the circuit board adjacent said first end, a fiber optic receptacle at the first end, electrical contacts at the second end connected to said circuit board, the electrical contacts for quickly installing and replacing said module to or from a circuit card assembly, a receptacle housing including a mounting panel with a connector port, a rail system for receiving the module and opposed to the connector port a second end, the second end including an electrical connector having signal contacts mating with the electrical contacts of the module, wherein upon mating of the module within the receptacle housing the electrical contacts of said transceiver module mate with the electrical connector of the receptacle a majority of the module is received within the receptacle and a gap is formed between the connector port and the module and a ground tab occupying the gap and providing an electrical connection from the conductive outside surface of the transceiver module in order to reduce electromagnetic interference and to provide for an FCC compliant module.

The transceiver module and receptacle assembly includes the ground tab mechanically attached to the transceiver module. The module and receptacle assembly includes a door hinged adjacent an edge of the receptacle housing wherein upon insertion of the module within the receptacle the door is opened and provides an effective open aperture at the first end of the receptacle and the electrically conductive outside surface of said transceiver module includes a portion of the first end of said transceiver module for reducing the effective open aperture when the first end is mounted within the open aperture created by the open door wherein the electrically conductive portion of said transceiver module is electrically connected to the ground tab of the receptacle in order to reduce electromagnetic interference and to provide for an FCC compliant module.

The transceiver module and receptacle assembly includes the ground tab formed of a thin, flexible metallic sheet having an apex that abuts against the connector port in order to provide grounding of the transceiver module to the receptacle. The transceiver module and receptacle assembly includes the transceiver module having an external surface that is metallized and upon insertion within the receptacle, the metallized transceiver module housing forms an electrical connection with the connector port in order to ground the transceiver module to the receptacle in order to provide for the harmless dissipation of static charge and provide for an FCC compliant module.

The transceiver module and receptacle assembly includes a pair of ground tabs attached to the sides of the transceiver module housing and make electrical and mechanical connection to the interior surface of the receptacle. The transceiver module and receptacle assembly includes a metallic optical receptacle assembly at the first end of the transceiver module housing. The transceiver module and receptacle assembly includes the transceiver connector a fiber optic plug receptacle. A transceiver module and receptacle assembly includes a circuit card connector which includes contacts arranged to allow for hot plugging and dissipation of static charge.

An optoelectronic transceiver receptacle is provided comprising a transceiver receptacle located on a circuit card of a communication system chassis and the communication system having components that generate and use timing signals or pulses at a rate in excess of 9,000 cycles per second, and the receptacle including a first end having a mounting panel formed of a conductive material and providing EMI shielding from radiating components on the circuit card, a first grounding means including a ground tab extending into the receptacle and mounted at second end of the receptacle, an electrical receptacle connector mounted at the second end of the receptacle, the electrical connector having a second grounding means, the electrical connector for coupling with electrical contacts of a removable optoelectronic transceiver module when a majority of the module is received within the receptacle and wherein ground for the transceiver circuit board is established upon insertion within the receptacle via a ground contact finger offset from a signal contact finger so that the ground contact finger mates with a corresponding ground contact finger prior to the mating of the signal contact finger with a corresponding signal contact finger wherein the first grounding means and the second grounding means provide for the harmless dissipation of static charge and provides for the proper sequencing of power and signal connections to facilitate hot plugging of the optoelectronic transceiver module.

The transceiver receptacle includes the ground tab mounted within the receptacle housing for the grounding of a conductive surface of a transceiver module. The transceiver receptacle includes the first grounding means having a ground surface protruding within the receptacle. The transceiver receptacle includes the ground surface attached to an arm which is molded within the receptacle housing. The transceiver receptacle includes the receptacle mounted therein and a guide rail for receiving a transceiver module.

The transceiver receptacle includes the guide rail having a detente for guiding the transceiver module along the guide rail. The transceiver receptacle includes a chassis faceplate within the mounting panel at the first end, the electrical receptacle connector opposed to the mounting panel at a second end, the receptacle being defined by the area between the first end and the second end, and a guide rail mounted in the receptacle between the first end and the second end, wherein the guide rail guides a transceiver module through the receptacle to align the transceiver module with the electrical receptacle connector. The transceiver receptacle includes a circuit card connector mounted to the circuit card that is mounted transverse to the mounting panel. The transceiver receptacle includes a pair of guide rails are mounted on the circuit card. The guide rail receives a frame member of a transceiver module housing.

A removable optoelectronic transceiver module is provided comprising, a transceiver module housing having a first end, a second end and an electrically conductive outside surface, a circuit board mounted within the housing and an optical subassembly electrically connected to the circuit board adjacent said first end, a fiber optic receptacle at the first end, electrical contacts at the second end connected to said circuit board and the electrical contacts for quickly installing and replacing said module to or from a circuit card assembly, a first retention member attached at the first end of the module and the retention member engaging a corresponding second retention member on the receptacle, and a ground tab occupying a gap formed between the module and a mounting panel of the receptacle and providing electrical connector from the conductive outside surface of the transceiver module to the mounting panel in order to reduce electromagnetic interference and to provide for an FCC compliant module.

The transceiver module includes the first retention member on the module having a protrusion and the second retention member on the receptacle is a recess. The transceiver module includes the second member having a pluggable connector having ground contacts offset from adjacent electrical contacts. The transceiver module includes first ground member that makes contact with a ground tab of the receptacle before signal contacts, in order to ground the module to the circuit ground and provide for static discharge. The transceiver module includes contacts of the pluggable connector arranged to allow the hot plugging.

A removable transceiver module and receptacle assembly further comprises a transceiver housing including a first end, a circuit board mounted within said transceiver housing and an electronic circuit connected to said circuit board adjacent said first end, an electrically conductive surface of said transceiver housing, an electrical connector at a second of said transceiver housing attached to said circuit board for quickly installing and replacing said module to or from a receptacle mounted to a circuit card assembly and the connector including metallic fingers to provide for hot plugging of the module wherein a ground contact is mated before a signal contact when the electrical connector is mated within the receptacle and the receptacle including a conductive mounting panel providing for EMI shielding of electromagnetically radiating components on the circuit card assembly and when a majority of the module is received within the receptacle the electrically conductive surface of the module is conductively coupled to the conductive mounting panel order to provide a reduction of electromagnetic emissions from the module and receptacle assembly and to provide an FCC complaint removable transceiver and receptacle assembly.

The optoelectronic module includes the ground contact protruding beyond the signal contact so that the ground contact will make an electrical connection before the signal contacts. The optoelectronic module includes the ground contact providing for static discharge. The optoelectronic module includes the ground contact establishing a reference potential. The optoelectronic module includes the electrical connector protruding perpendicularly from an end face of the second end and parallel to the circuit board. The optoelectronic module includes a plurality of metallic fingers extending from said housing on opposed sides of an insulator. The optoelectronic module includes a mounting member for facilitating the insertion and removal of said module to and from a circuit card assembly. The removable optoelectronic module includes the circuit card assembly having a circuit card connector for receiving the electrical connector of the module, the circuit card connector having circuit card ground contacts offset from circuit card signal contacts so that the ground contact of the module connector is mated with the circuit card ground contacts before the signal contact of the module connector is mated with the circuit card signal contacts.

The electrical connector includes the circuit board forming the electrical connector and includes the metallic fingers formed of a conductive material affixed to the circuit board. The electrical connector includes a shroud protruding from the second end of the housing surrounding the distal end of the circuit board. The electrical connector of includes the circuit board including circuitry mounted thereon which is connected to a plurality of contacts. The electrical connector includes the housing having a shroud protruding from the second end.

In a still further form of the invention, an optoelectronic transceiver module and receptacle assembly for receiving a removable optoelectronic transceiver module is provided, the assembly comprising the optoelectronic transceiver module including an electrically conductive outside surface, a transceiver receptacle located on a circuit card of a communication system chassis for receiving a majority of the module therein and the receptacle including a first end having a mounting panel formed of a conductive material and providing EMI shielding from radiating components on the circuit card and an electrical connector mounted at the second end of the receptacle and the electrical connector having a grounding means, the electrical connector for receiving the removable optoelectronic transceiver module.

A transceiver receptacle is provided comprising a transceiver receptacle located on a circuit card of a communication system chassis and the receptacle including a first end having a mounting panel formed of a conductive material and providing EMI shielding from radiating components on the circuit card and a grounding tab configured to occupy a gap between an electrically conductive surface of a removable transceiver module and the mounting panel and the receptacle includes at a second end an electrical receptacle connector for receiving a connector of the removable transceiver module wherein upon mating of the receptacle connector with the removable transceiver module connector a majority of the removable transceiver module is received within the receptacle.

The transceiver receptacle including the mounting panel providing for shielding and not for static discharge purposes. The transceiver receptacle including the grounding tab abuts against an electrically conductive outer surface of the module in order to ground the module and reduce electromagnetic interference and provide for an FCC compliant module. The transceiver receptacle including the removable transceiver module having a transceiver connector having an electrical plug receptacle. The transceiver receptacle including the removable transceiver module having a media transducer having an electrical plug receptacle and an electrical subassembly.

Various means for practicing the invention and other advantages and novel features thereof will be apparent from the following detailed description of an illustrative preferred embodiment of the invention.

BRIEF DESCRIPTION OF THE DRAWINGS

There is shown in the drawings a preferred embodiment of the present invention, wherein like numerals in the various figures pertain to like elements, and wherein:

FIG. 3 is a bottom perspective view of the optoelectronic transceiver module depicted in FIG. 1;

FIG. 4 is an enlarged perspective view of the potting box used in the manufacture of the optoelectronic module depicted in FIGS. 1–3;

FIG. 5 is a perspective view of the recess cover used with the potting box of FIG. 4;

FIG. 6 is another enlarged perspective view of the potting box of FIG. 4;

DETAILED DESCRIPTION OF THE PRESENTLY PREFERRED

Figure 1:
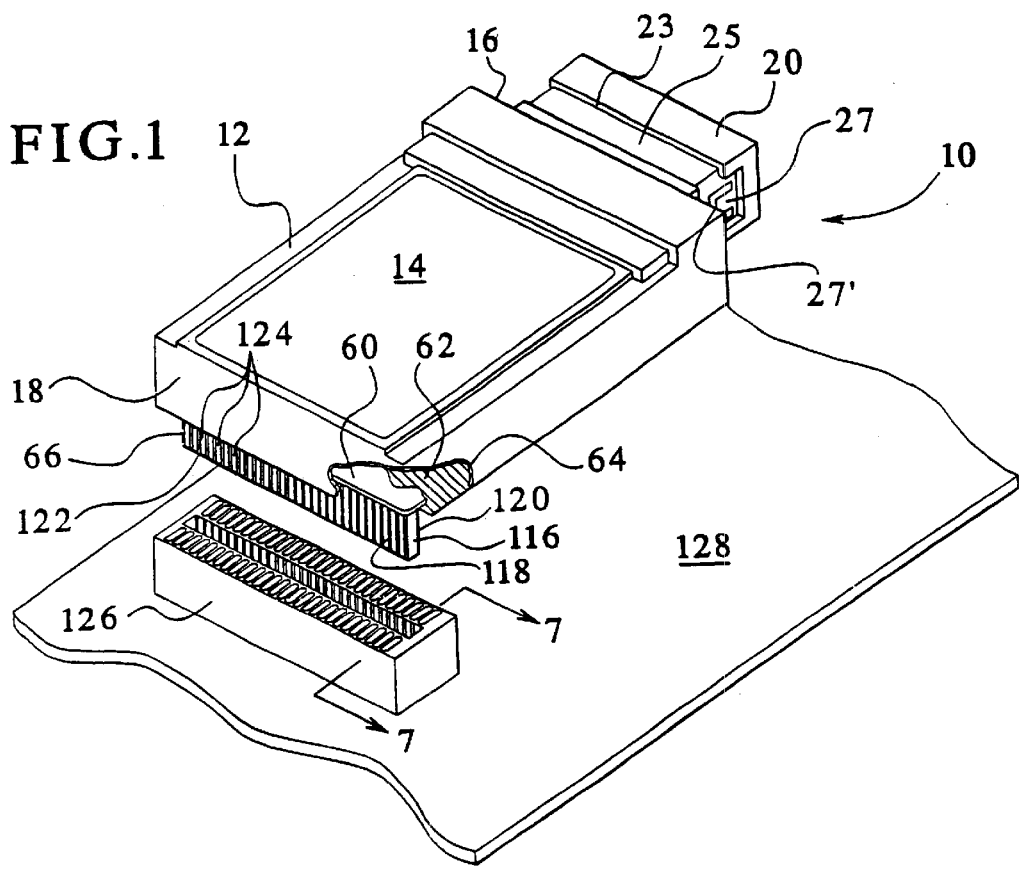
FIG. 1 is an enlarged perspective view of an optoelectronic transceiver module in accordance with the present invention and having a partial fragmentary view depicting the module's circuit board and potting material.

Referring to the drawings, and particularly to FIG. 1, an enlarged perspective view of an optoelectronic transceiver module 10 in accordance with the present invention is depicted. The module 10 has a main housing 12 which generally has the shape of an oblong box. The main housing 12 has a generally rectangular top 14 with a first end 16 and an opposite second end 18 extending perpendicularly from the top. Attached to the first end 16 of the main housing 12 is a transceiver connector 20 for receiving fiber optic plugs.

Figure 2:
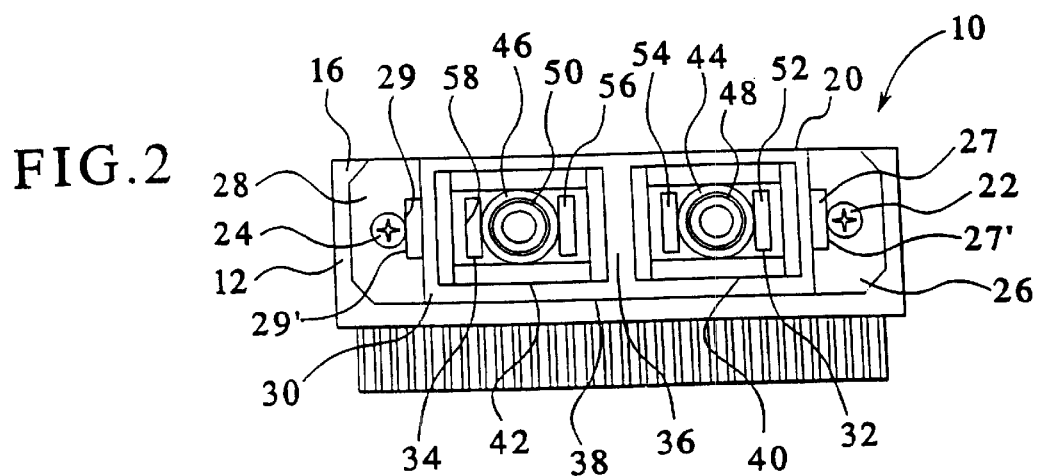
FIG. 2 is a front view of the optoelectronic transceiver module depicted in FIG. 1.

Turning to FIG. 2, a front view of the optoelectronic transceiver module 10 is depicted. The transceiver connector 20 is attached to the first end 16 of the main housing 12 by two screws 22,24. The two screws 22,24 extend through the transceiver connector's mounting ears 26,28 and into the main housing 12. Extending perpendicularly from the mounting ears 26,28 is a generally rectangularly shaped connector shell 30. The connector shell 30 provides two receptacles 32,34 for receiving fiber optic connector plugs. The receptacles 32,34 are formed by the connector shell 30 along with a divider wall 36 which extends along the center of the connector shell. Furthermore, located in the bottom 38 of each receptacle 32,34 is a keying channel 40,42 which extends toward the first end 16 of the main housing.

In the preferred embodiment, the receptacles 32,34 of the connector shell 30 are specifically dimensioned to receive an SC duplex plug. Therefore, the keying channels 40,42 ensure that an SC plug will be inserted so that receptacle 32 will only accept a plug for sending data and receptacle 34 will only accept a plug for receiving data.

Extending from the main housing 12 and into each of the receptacles 32,34 is an optical subassembly 44,46. As previously indicated, the optical subassembly 44 is for sending transmissions over a data link and the optical subassembly 46 is for receiving transmissions over a data link. In order to facilitate the connection between the transceiver and the data links, each optical subassembly has a ferrule receiving portion 48,50. The ferrule receiving portion 48,50 couples with the SC plug. Furthermore, the transceiver's latch members 52,54,56, and 58 firmly hold the SC plug in contact with connector 20.

The actual sending and receiving of optically encoded data is performed by a laser diode within the optical subassembly 44 and a photo diode within the optical subassembly 46. Both the laser diode and the photo diode are electrically connected to a circuit board which is mounted within the main housing 12.

Turning back to FIG. 1, a portion of the circuit board 60 is depicted. Incorporated onto the circuit board 60 is circuitry for transmitting and receiving optically encoded data (circuitry not shown). The circuit board 60 is encased in potting material 62 and a potting box 64 which forms the main housing 12. The potting material 62 encases the circuit board 60 such that only the circuit board's male ribbon style connector 66 extends from the potting material 62.

Turning to FIG. 3, a perspective view of the bottom 68 of the transceiver module 10 is depicted. In the preferred embodiment, the bottom 68 has two mounting ports 70,70 which are adjacent to the first end 16 of the main housing 12. In addition, the male ribbon style connector 66 protrudes perpendicularly from the bottom 68 and is adjacent to the second end 18 of the main housing 12.

In an alternative embodiment, the ribbon style connector 66 may protrude perpendicularly from the second end 18 of the module 10 so that it can be connected to a circuit card assembly in a direction which is parallel to the direction of insertion of the optic plugs into the module's receptacles. However, in this alternative embodiment, another recess cover will be needed in order to prevent potting material from escaping the second end of the potting box.

Referring to FIG. 4, an enlarged perspective view of the optoelectronic module's potting box 64 is depicted. The potting box 64 forms the outer housing of the optoelectronic module. Thus, the potting box generally has the shape of an oblong box with a rectangular bottom 72, two parallel side walls 74,74, a first end wall 76, and an opposite second end wall 78. In a preferred embodiment, the potting box 64 is injection molded of a polymer material such as VALOX, STANYL, or any other glass-filled heat resistant material which can withstand solder reflow temperatures. The use of such a potting box eliminates the need for a silicone mold required by prior art modules.

In addition, it is preferred that the potting box 64, including the latch members 52,54,56, and 58, be either plated, wet plated, or vacuum metalized with an aluminum or stainless steel coating in order to dissipate an electrostatic discharge and provide for electromagnetic shielding. As well, the transceiver connector 20 (FIG. 1) may be either plated, wet plated, or vacuum metalized, in order to reduce emissions and enhance grounding of the module. Such metalization of the connector 20 can bring the module in compliance with FCC Rules, Part 15. In a preferred embodiment, the connector 20 is metalized separately from the potting box 64 so that each attachment portion is metalized and provides for conductivity between the parts. As the connector 20 will be attached to a chassis containing fiber optic connectors which are at ground potential, the connector will ground the metalized potting box 64 which is attached to a daughter board. Such grounding enhances the module's ability to dissipate electrostatic discharge and provide for electromagnetic shielding. The transceiver connector 20 also includes a grounding clip 25 attached at the slot 23.

As also shown in FIGS. 1–3, the transceiver connector 20 includes a grounding clip 25 attached at the slot 23 in the connector 20. The grounding clip 25 serves as a means for forming an electrical connection with an externally grounded structure such as a computer chassis. Correspondingly, the grounding clip 25 is made of a metallic material, such as stainless steel, and includes two tabs 27,29 which protrude from each side of the connector 20. The tabs 27,29 are generally rectangular in shape with only one side of each tab being united to the grounding clip 25. Correspondingly, each tab 27,29 has a respective distal end 27',29' which extends away from the connector 20. In a preferred embodiment, the connector 20 is first metalized and then the ground clip 25 is attached so that an electrical conductive path is maintained between the grounding clip 25 and the connector 20.

Figure 2A:
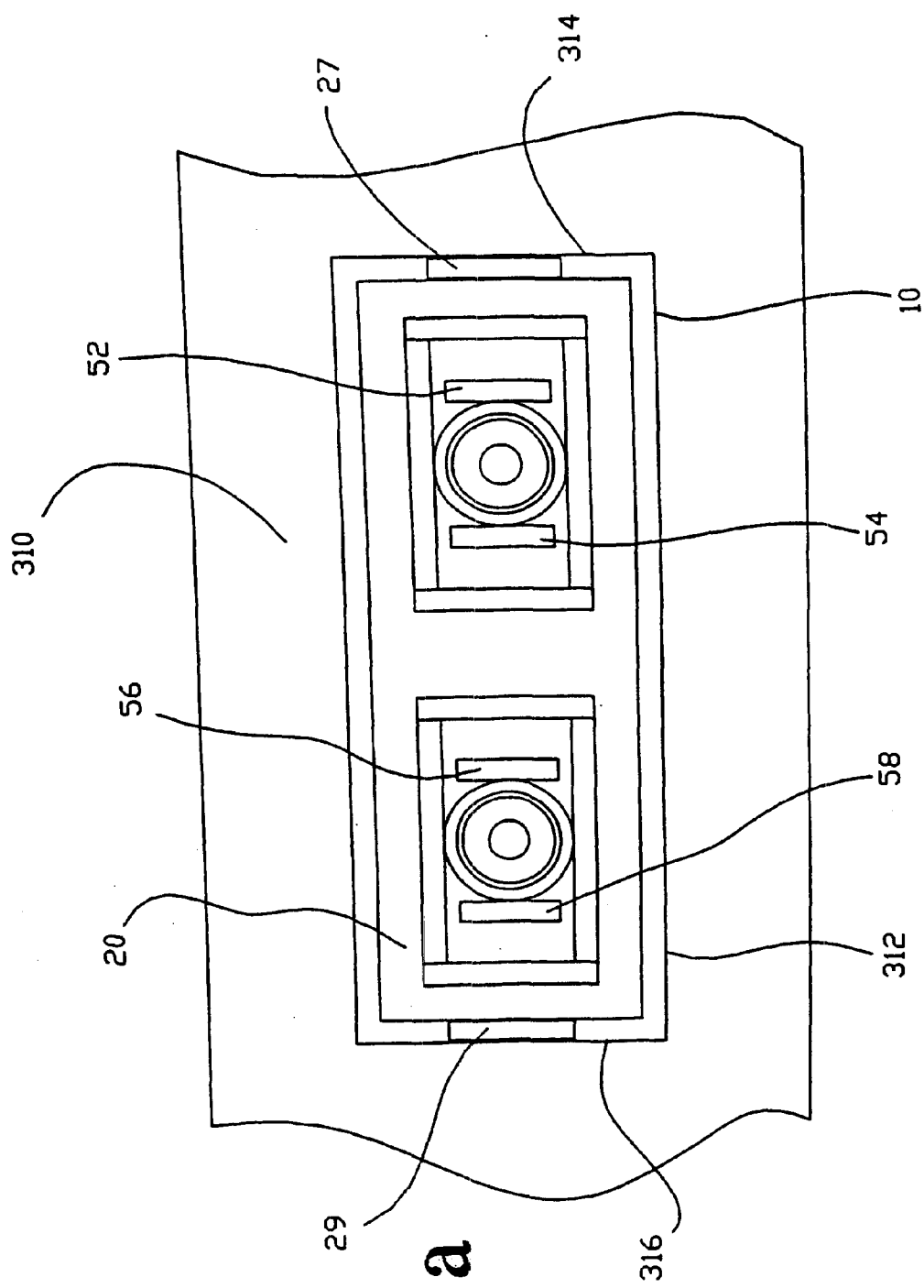
FIG. 2a is a front view of a grounded computer chassis with the optoelectronic transceiver module of FIG. 2 extending through a connector port within the computer chassis.

Moving to FIG. 2a, a front view of the outside of a grounded computer chassis 310 is depicted with the connector 20 of the optoelectronic transceiver module 10 extending through a connector port 312 within the computer chassis. As commonly known in the art, the computer chassis 310 is typically made of a conductive metallic material and is tied to a ground potential (i.e., grounded) by conventional means. Furthermore, the chassis provides a connector port 312 for each optoelectronic transceiver module mounted within the computer chassis (only one connector port and one transceiver module is depicted in FIG. 2a). The connector port 312 consists of an opening which is dimensioned so that the transceiver module connector 20 can extend through the connector port. Therefore, the transceiver module 10 can be mounted within the chassis 310 with a computer with the transceiver module connector 20 extending from, and being readily accessible from, the outside of the computer chassis.

Correspondingly, when the transceiver module connector 20 is positioned within the connector port 312, the tabs 27,29 will press against the sides 314,316 of the connector port. Consequently, the tabs 27,29 will form an electrical connection with the computer chassis which will result in the transceiver module connector 20 becoming grounded. In addition, the entire metalized potting box, including the metalized latch members 52,54,56, and 58, will become grounded since, as indicated previously, the transceiver module connector 20 is conductively attached to the potting box.

Correspondingly, a means of pre-grounding an SC connector is provided by the grounded latch members 52,54,56, and 58. For example, as an SC connector is attached to the transceiver module 10, the housing of the SC connector will first abut against one of the ground latch members 52,54,56, and/or 58. Accordingly, any static charge on the SC connector will be removed by the grounded latched members via the conductive electrical path from the potting box, to the transceiver connector, its corresponding grounding clip, and then to the grounded computer chassis via the tabs 27.

As previously indicated, all of the transceiver's latch members 52, 54, 56, and 58 extend from the first wall 76 of the potting box 64. Also, the first end wall 76 of the potting box furnishes the mounting ports 70,70 which are located on the bottom of the main housing. In a preferred embodiment, the latch members 52, 54, 56 and 58 are integrally molded with the potting box 64.

Circuit board standoff columns 80 are also provided by the potting box 64 (only one standoff column is depicted in FIG. 4). Each standoff column protrudes from the bottom 72 of the potting box 64 and is positioned next to the first end wall 76 and one of the side walls 74,74 for supporting the circuit board 60. The standoff columns 80 have a length equal to approximately half the depth of the potting box 64 with the distal end of the column having a circuit board mounting port 82.

As depicted in FIG. 4, the first wall 76 of the potting box 64 has a recess 84 for allowing the placement of the circuit board's optical subassemblies. The recess 84 has two semicircular through-ports 86,86. Within each through-port 86,86 are two guide beams 88,90 which are positioned on each end of the through-port's semicircle for positioning the optical subassemblies 44,46.

Also located on the first wall 74 are two recess cover alignment guide beams 92,94. The alignment guide beams 92,94 border each side of the recess 84 and extend along the entire depth of the recess. The bottom of the recess 84 has three flat mating surfaces 95 (only two of the mating surfaces are depicted in FIG. 4).

Correspondingly, referring to FIG. 5, a recess cover 96 is depicted for placement within the recess located in the first wall of the potting box. Preferably, the recess cover 96 is made of the same material as the potting box and is either plated, wet plated, or vacuum metalized with an aluminum or stainless steel coating.

In FIG. 5, the recess cover 96 has two semicircular through-ports 98,100. Within each of the through-ports 98,100 are two guide beams 102,104 positioned on each end of the through-port's semicircle. Also, the top of the recess cover includes three flat mating surfaces 105.

The recess cover 96 firmly mounts within the recess of the potting box's first wall so that the mating surfaces 95 and 105 of both the recess 84 and the recess cover 96 will abut each other. The recess cover 96 includes three indentions 106 which allow the cover to be positioned around the location where the latch members 52, 54, 56, and 58 attach to the potting box. In addition, on each end of the recess cover 96 there are alignment grooves 108,110 which provide for sliding engagement with the alignment guide beams 92,94 bordering the recess within the potting box's first wall.

Referring back to FIG. 4, during the manufacture of the transceiver module the circuit board is placed in the potting box 64 with the male ribbon connector protruding outside of the potting box and the circuit board's optical subassemblies protruding out of the recess 84 in the first wall 76. The optical subassemblies 44,46 are properly positioned within the potting box 64 by the alignment guides 88,90 located within each through-port 86,86.

Once positioned within the potting box 64, the circuit board 60 is affixed by two screws which are mounted to the standoff columns 80 via the circuit board mounting ports 82.

Once the circuit board 60 is secured within the potting box 64, the recess cover 96 is mounted onto the first end wall 76. The recess cover 96 is mounted by engaging its alignment grooves 108,110 with the potting box's recess cover alignment guide beams 92,94. When the recess cover 96 is slid into position, the cover's through-ports 98,100 and associated alignment guide beams 102,104 will adjoin the circuit board's optical subassemblies 44,46. Furthermore, due to the tight tolerances of both the potting box 64 and the recess cover 96, a liquid tight seal will be formed between the potting box 64, the recess cover 96, and the optical subassemblies 44,46. Thus, with the recess cover 96 in place, potting material is injected within the potting box 64 for encasing the circuit board 60. The time to mold the module by the above method is reduced by approximately 90% over the prior art molding process because no hand caulking is needed to form the liquid tight seal.

Finally, referring to FIG. 6, the connector shell 20 (See FIGS. 1 & 2) is mounted onto the first end wall 76 of the potting box 64 after the potting material has cured. Alignment of the connector shell 20 is provided by two mounting posts 112,112. Each mounting post 112 has a bore 114 which facilitates the attachment of the connector shell 20, by the use of the previously mentioned screws, onto the potting box 64.

In an alternative embodiment, the ribbon style connector 66 may protrude perpendicularly from the second end 18 of the module 10 so that it can be connected to a circuit card assembly in a direction which is parallel to the direction of insertion of the optic plugs into the module's receptacles. However, in this alternative embodiment, another recess cover will be needed in order to prevent potting material from escaping the second end of the potting box.

Referring back to FIG. 1, the male ribbon style connector 66 protruding from the module 10 has a beam portion 116, made of insulative material, which extends perpendicularly across the length of the circuit board 60. The male ribbon style connector 66 also has a first side 118, an opposite second side 120, and a distal end 122. Extending perpendicularly from the circuit board 60 on both the first side 118 and the second side 120 of the male ribbon style connector 66 are twenty-eight electrical contacts 124. Each electrical contact 124 consists of a strip of conductive material which is affixed to the male ribbon style connector 66 and is electrically connected to the circuitry mounted on the circuit board 60.

Figure 7:
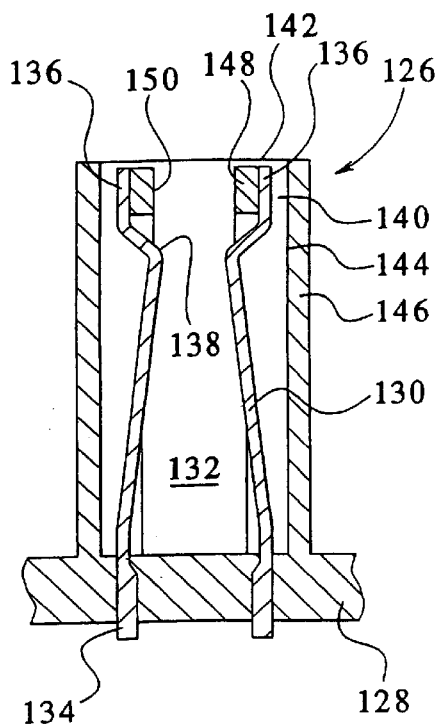
FIG. 7 is an enlarged cut-away side view of the female ribbon style connector taken along line 7—7 of FIG. 1.

Correspondingly, the male ribbon style connector 66 couples to a female ribbon style connector 126 which is mounted onto the circuit card assembly 128. Referring to FIG. 7, an enlarged cut-away side view is shown of the female ribbon style connector 126 taken along line 7—7 of FIG. 1. The female ribbon style connector 126 has two parallel rows of twenty-eight (28) contact beams 130,130 contained within a contact chamber 132 (only one contact from each row is depicted). Each contact beam 130 is constructed of a flat strip of conductive metallic material. Furthermore, each contact beam 130 has a first end 134, a second distal end 136, and a bend 138 which is located adjacent to the second end and extends toward the contact beam located in the opposite row.

The female ribbon style connector 126 is mounted onto the circuit card 128 such that the first end 134 of each contact beam 130 extends through the circuit card assembly. Likewise, the second end 136 of each contact beam 130 extends within a travel limitation slot 140 formed in the top 142 of the female ribbon style connector 126. Each slot 140 provides a backstop 144, consisting of one of the connector's walls 146, and a frontstop 148. Correspondingly, contact beams 130,130 are positioned in the chamber 132 such that the second end 136 of each contact beam 130 resiliently urges against the frontstop 148.

In order to provide access to the contact beams 130,130 within the female ribbon style connector 126, the top 142 of the connector has a slot 150 positioned between the two rows of contact beams. Correspondingly, in order to make an electrical connection between the female ribbon style connector 126 and the male ribbon style connector 166 depicted in FIG. 1, the distal end 122 of the male ribbon style connector is inserted within the female connector's slot 150. As the male ribbon style connector 66 is pushed further within the female connector's chamber 132 the two rows of contact beams 130 will be forced to separate further from each other. In addition, each contact beam 130 will resiliently urge against a corresponding electrical contact 124 mounted on the male ribbon style connector 66. Thus, an electrical connection will be formed between the male ribbon style connector's electrical contacts 124,124 and the female connector's contact beams 130,130.

Similarly, to disconnect the male ribbon style connector's electrical contacts 124,124 from the female connector's contact beams 130,130 the male connector 66 is simply pulled from the chamber 132 of the female connector. Once the male ribbon style connector 66 has been removed from the chamber 132, the contact beams 130 of the female connector 126 will resiliently regain the configuration of FIG. 7, whereby the second end 136 of each contact beam will abut its corresponding frontstop 148.

Figure 8:
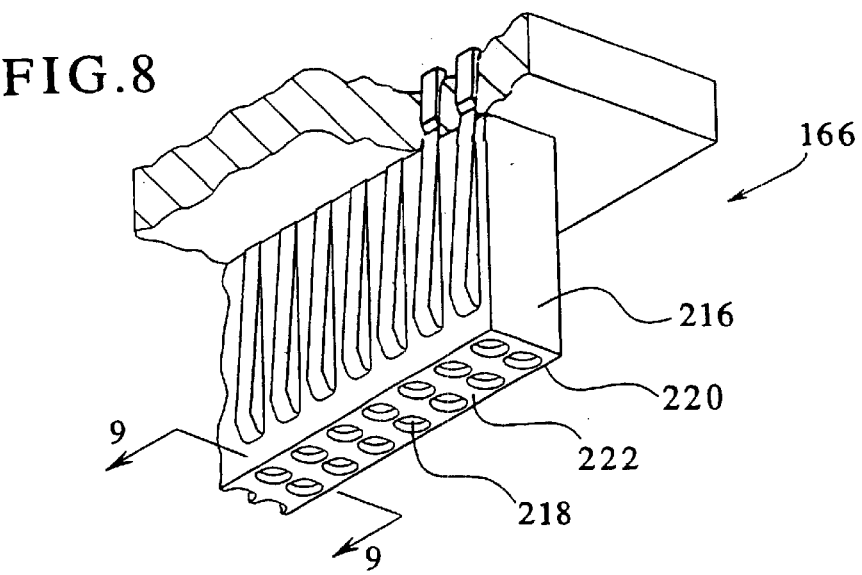
FIG. 8 is an enlarged perspective view, along with a partial fragmentary view, of a resilient male ribbon style connector for use with the optoelectronic transceiver module of FIGS. 1–3.

Turning to FIG. 8, an enlarged perspective view, along with a partial fragmentary view, is depicted of a resilient male ribbon style connector 166. The connector 166 includes a beam type housing 216 having a first side 218, an opposite second side 220, and a distal end 222. The resilient male ribbon style connector 166 in FIG. 8 serves as another embodiment of the male ribbon style connector depicted in FIGS. 1–3 wherein the male connector in FIG. 8 is resilient and the male connector in FIGS. 1–3 is non-resilient. It should be noted, however, that other means for quickly installing and replacing the module from a circuit card assembly may be used.

Figure 9:
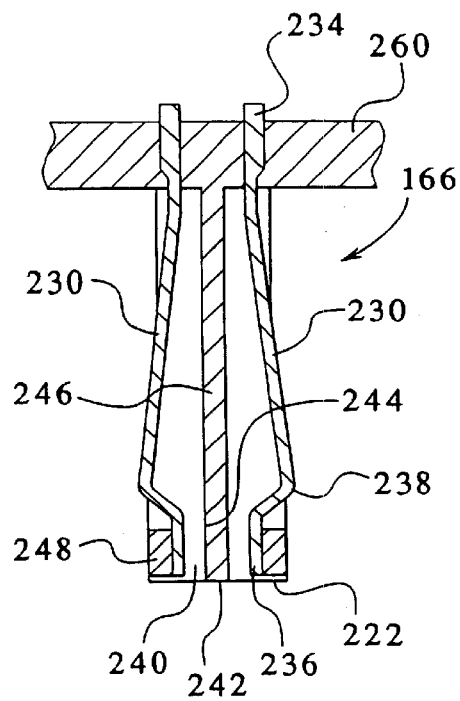
FIG. 9 is a cut-away side view of the resilient male ribbon style connector taken along line 9—9 of FIG. 8.

Referring to FIG. 9, an enlarged cut-away side view of the resilient male ribbon style connector 166 is shown taken along line 9—9 of FIG. 8. The male ribbon style connector 166 has two parallel rows of twenty-eight (28) contact beams 230, (only one contact from each row is depicted). Each contact beam 230 is constructed of a flat strip of conductive metallic material. Furthermore, each contact beam 230 has a first end 234, a second distal end 236, and a bend 238 which is located adjacent to the second end and extends away from the contact beam located in the opposite row.

The male ribbon style connector 166 is mounted onto the module's circuit board 260 such that the first end 234 of each contact beam 230 extends through the circuit board. In a preferred embodiment, the first end 234 of the contact 230 is inserted within a through-hole of the circuit board 260 which contains traces for providing an electrical connection from the contact 260 to components mounted on the board. Likewise, the second end 236 of each contact beam 230 extends within a travel limitation slot 240 formed in the top 242 of the resilient male ribbon style connector 166. Each slot 240 provides a backstop 244, consisting of the connector's support wall 246, and a frontstop 248. Corresponding, contact beams 230,230 are positioned such that the second end 236 of each contact beam 230 resiliently urges against the frontstop 248.

Access for making an electrical connection with the contact beams 230,230 is provided since they protrude from the male ribbon style connector 166 in the area around the bends 238,238. Correspondingly, in order to make an electrical connection between a female ribbon style connector and the resilient male ribbon style connector 166, the distal end 222 of the male ribbon style connector is inserted within a slot provided by the female connector. As the male ribbon style connector 166 is pushed within the female connector, the two rows of contact beams 230,230 will be forced to compress towards each other. In addition, each contact beam 230 will resiliently urge against a corresponding electrical contact mounted within the female ribbon style connector. Thus, an electrical connection will be formed between the male ribbon style connector's electrical contact beams 230, 230 and the female connector's contact beams.

Similarly, to disconnect the resilient male ribbon style connector 166 from the female connector, the male connector is simply pulled from the female connector. Once the male ribbon style connector 166 has been removed, the contact beams 230,230 will resiliently regain the configuration of FIG. 9, whereby the second end 236 of each contact beam will abut its corresponding frontstop 248.

Figure 10:
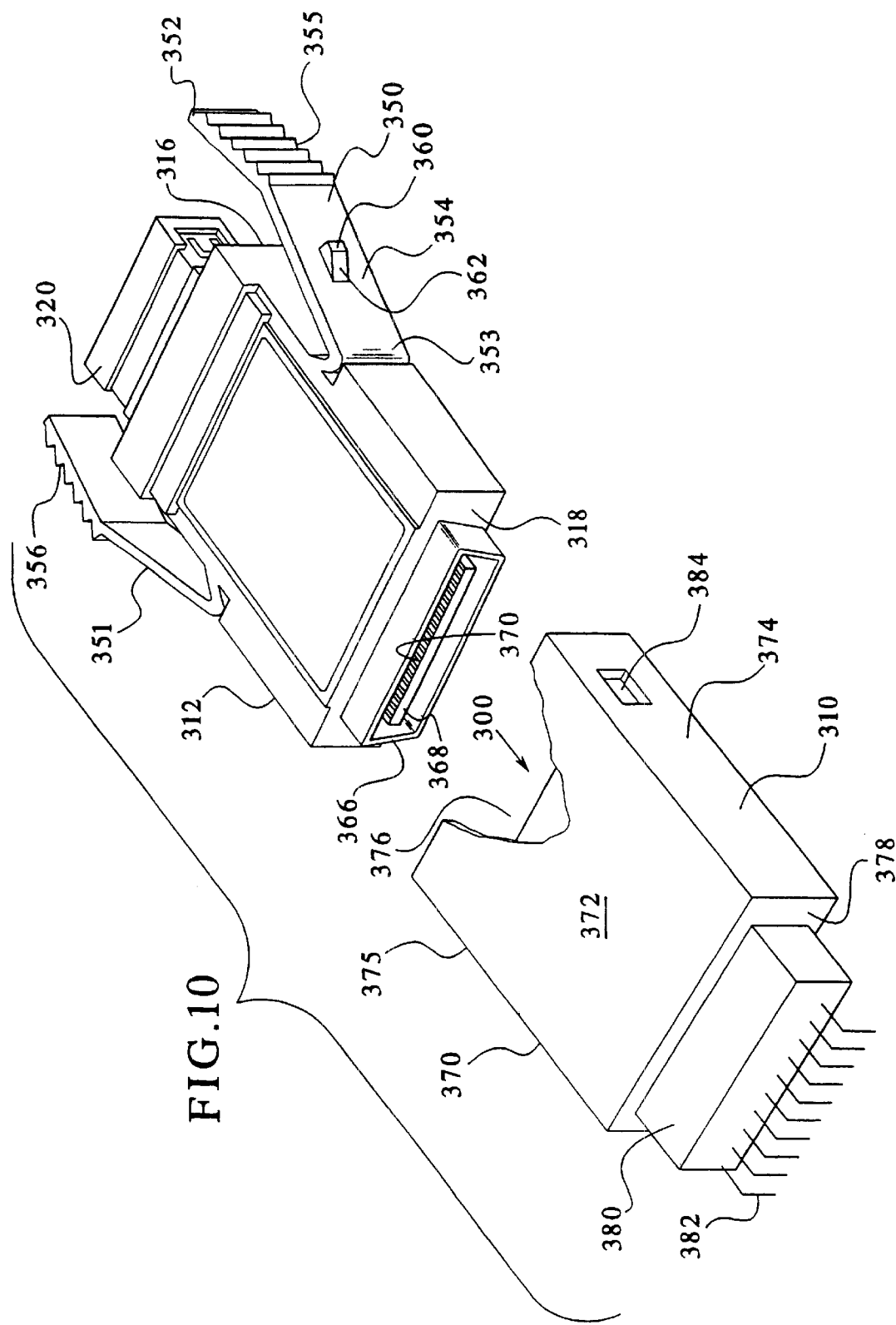
FIG. 10 is a plan view of the alternative embodiment shown in FIG. 10 but in a mated orientation.

An alternative embodiment of the present invention is shown in FIG. 10 having a main housing 312, having a first end 316 and a second end 318. As discussed in the previous embodiments, the housing 312 includes optical subassemblies for sending transmission over a data link and receiving transmissions over a data link. The preferred embodiment is an optoelectronic transceiver, however, a simplex transmitter or receiver or multiple transmitters or receivers may be incorporated in the module housing of the alternative embodiment. At the first end 316 is a transceiver connector 320 for receiving fiber optic plugs. In an alternative embodiment, optical fibers may be directly attached to the module and the optical subassemblies therein. At the second end 318 is a pluggable connector 366. In the preferred embodiment, the pluggable connector 366 is a D-shaped connector having a printed circuit board 368 having multiple contact traces 370 adhered thereto. The transceiver housing 312 is pluggable into receptacle 310 and is inserted into the receptacle 310 in direction of arrow 300. The receptacle 310 includes a receptacle housing 370 having a top 372 and sides 374,375. The receptacle housing 370 includes an open end 376 and a closed end 378. At the closed end 378 of the receptacle housing 370 is a connector 380 for mating with the pluggable connector 366. The connector 380 protrudes into the interior the receptacle housing 370 and has an aperture for receiving the pluggable connector 366 of the transceiver housing 312. In the preferred embodiment, the connector 380 is a female connector for receiving the male connector 366. However in an alternative embodiment, the pluggable connector 366 of the transceiver housing 312 maybe a female connector and the connector 380 of the receptacle housing 370 would be a male connector. Protruding from the connector 380 are contacts 382 for direct connecting to a printed circuit board in a peripheral device such as a work station or computer to wire the connector 380 directly to traces of a printed circuit board. In an alternative embodiment, a flat ribbon cable for transmitting the electrical signals protrudes from the transceiver module. The receptacle housing 370 includes in sides 374,375 aperture 384 for providing the locking of the transceiver within the receptacle housing 370.

The transceiver housing 312 includes a pair of release levers 350,351. The description of release lever 350 is the same of that for 351. The release lever 350 includes a first end 353 which is attached to the side of the transceiver housing 312. In a preferred embodiment, the release lever 350 is integrally molded with the transceiver housing 312. The release lever 350 includes a second end 352 which includes a gripping portion 355 which has lined edges to assist in gripping of the release lever 350. Intermediate to the first end 353 and the second end 352 is an intermediate portion 354. The intermediate portion 354 angles outwardly away from the sides of the transceiver housing 312. Attached at the end of the intermediate portion 354 is the second end 352 which is generally parallel to the side of the transceiver housing 312. However, as the intermediate portion 354 angles outward and away from the side of the transceiver housing 312, the second end 352 is at a distance from the sides of the transceiver housing 312 in its nonmated condition. Protruding from the intermediate portion 354 is detente 360. The detente 360 includes an engagement surface 362. Upon insertion of the transceiver housing 312 into the receptacle 370, the intermediate portion 354 abuts against the side 374 of the receptacle housing 370 and causes the release lever 350 to compress inwardly toward the housing 312. As the housing 312 is further inserted within the receptacle, the engaging portion 362 abuts against the sidewall 374 of the receptacle housing 370 causing the release lever 350 to compress further. Upon further insertion, the detente 360 engages aperture 384 of the receptacle housing 370 and the release lever 350 snaps outwardly to engage the aperture 384. Upon snapping outwardly of the release lever 350, the transceiver housing 312 is fully mated within the receptacle housing 370. In this fully mated position, the pluggable connector 366 is fully mated with the connector 380 of the receptacle housing 370.

For removal of the transceiver housing 312 from the receptacle housing 370, the release levers 350,351 are grasped at the gripping portion 355 of the second end 352 in order to compress the levers inwardly toward the transceiver housing 312. The compression of the release levers 350 releases the detente 360 from the aperture 384 of the receptacle housing 370. Allowing the pluggable connector 366 of the transceiver housing 312 to be removed from the connector 380 of the receptacle housing and for the entire transceiver housing 312 to be removed from the receptacle 370.

Figure 11:
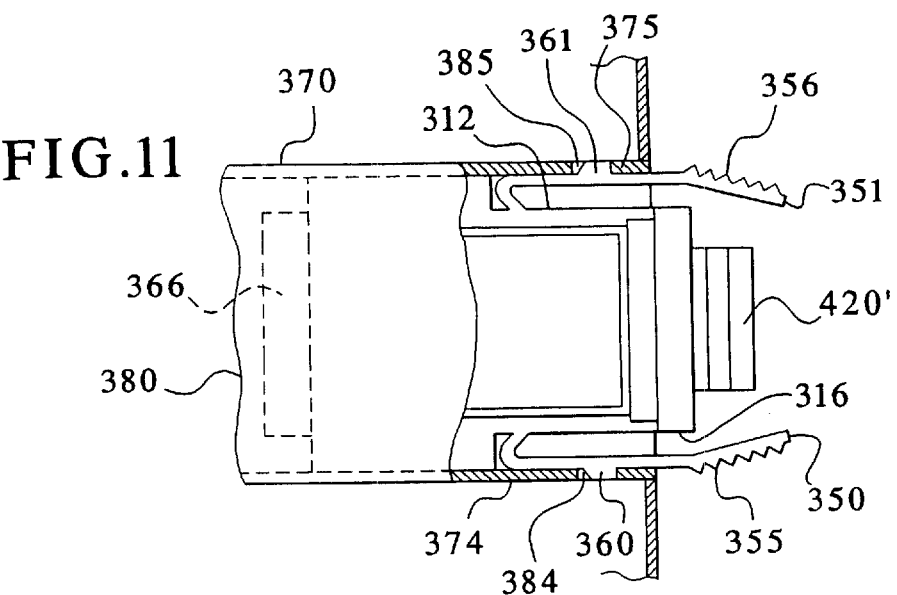
FIG. 11 is a plan view of an alternative embodiment of a transceiver module having an electrical interface of the present invention.

Turning to FIG. 11, a top view of the alternative embodiment of the transceiver of the present invention is shown mated within a receptacle. The transceiver housing 312 is mated within receptacle housing 370. The release levers 350,351 are compressed within the sidewalls 374,375 of the receptacle housing 370. The detentes 360,361 of the release levers 350,351, respectively, are seated within the apertures 384,385. In the fully mated position, the pluggable connector 366 is mated with the connector 380 of the receptacle housing 370. It can be seen that in order to release the transceiver housing 312 from the receptacle 370, the gripping portions 355,356 of the release levers 350,351 are protruding from the receptacle housing 370 and may be grasped between two fingers and compressed together in order to release the detentes 360,361 from the apertures 384,385 and to then release the transceiver from the receptacle.

Figure 12:
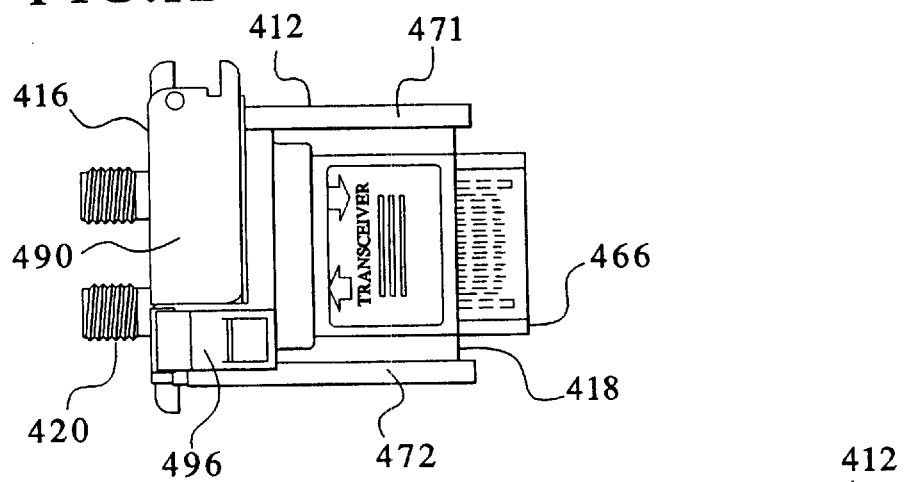
FIG. 12 is an enlarged perspective view of an end of the transceiver module of FIG. 12.

Still referring to FIG. 11, transceiver connector 420' is shown attached to the first end 316 of the transceiver module housing 312. In this alternative embodiment, the transceiver connector 420' may have an electrical connection and receive electrical plugs. As an alternative to the transceiver connector 320 shown in FIG. 10 which was described to receive fiber optic plugs, the transceiver connector 420' of FIG. 11 may receive electrical plugs. For example, a copper wired electrical connector may be inserted in the transceiver connector 420 having a receptacle opening for receiving the electrical plug therein (see also FIG. 12). In the alternative embodiment, the copper transceiver module housing 312 will not have optical subassemblies mounted therein. However, an electrical subassembly for the transceiver described above is still contained within the transceiver module, such as a transformer or other AC coupling means and differential (balanced) or single ended (unbalanced) transmission line drive and receive circuits. By providing a transceiver module 312 which supports different types of media in a common housing design, the transceiver module may be easily upgradable in the field. For example, an initial installation of an optical transceiver module (as shown in FIG. 12) having multi-mode capabilities could provide transmission distances of approximately 500 meters. Should the system be reconfigured so that the required transmission distances decrease to 20 to 30 meters, the multi-mode optical transceiver could easily be replaced with a less costly copper transceiver (as shown in FIG. 11) using the removable housing of the present invention. Such an operation can be easily accomplished by a technician in the field due to the easily disengageable latching means 350 and the pluggable connector 366 of the transceiver housing 312 and other features of the present invention discussed herein. Additionally, further upgrades may be accomplished in later reconfigurations that may require transmission distances of up to 10 kilometers by replacing the transceiver module with an optical transceiver module of the present invention having single-mode capabilities.

Referring to FIG. 12 a copper transceiver as discussed above is disclosed. The transceiver module housing 412 includes first end 416 and second end 418. Running between the first and second end along the sides of the transceiver housing 412 are rails 471, 472 for mounting to the guide rails of the receptacle assembly as disclosed in FIG. 14. The second end 418 of the transceiver housing is inserted into a receptacle assembly, such as shown in FIGS. 14–17, and pluggable connector 466 provides electrical connection to the receptacle assembly and a motherboard. The first end 416 includes a latch cover 490 to latch the transceiver housing 412 to the receptacle assembly, as discussed in more detail below. The latch cover 490 also includes latch member 496. Mounted at the first end 416 are a pair of transceiver connectors 420. In the embodiment of FIG. 12 the transceiver connectors are copper connectors for receiving electrical coaxial cable such as an SMA connector.

Figure 13:
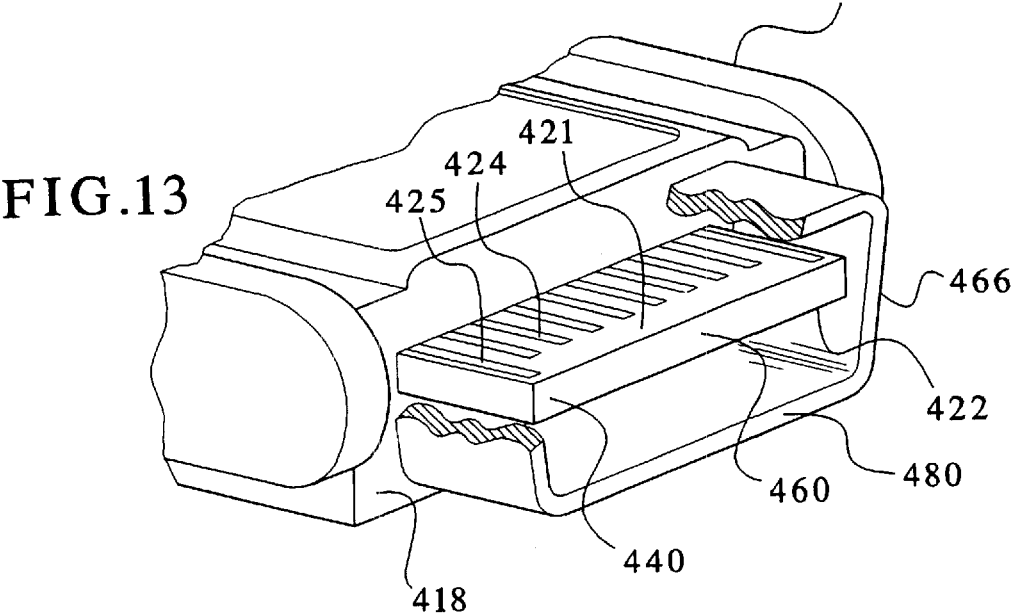
FIG. 13 is a perspective view of an alternative embodiment of a transceiver module of the present invention mounted to a receptacle assembly.

Turning to FIG. 13, an enlarged perspective view of the second end 418 of the transceiver housing 412 is disclosed. The pluggable connector 466 or male ribbon style connector includes a D-shaped shroud 480 encircling an insulative substrate 460 such as a circuit board. The circuit board 460 protruding from the transceiver housing 412 has a first side 421, an opposite second side 422, and a distal end 440.

Extending perpendicularly from the second end 418 of the transceiver housing 412 is circuit board 460 having affixed on both the first side 421 and the second side 422 twenty electrical contacts 424. Each electrical contact 424 consists of a strip of conductive material which is affixed to circuit board 460 and is electrically connected to the circuitry mounted on the circuit board 460 within the transceiver module 412. The first side 421 of the circuit board 460 includes ten electrical contacts 424 affixed thereto. As shown in FIG. 13 the electrical contacts are numbered 1 through 10. The first and tenth contact adjacent the side edges of the circuit board 460 are ground contacts 425. The ground contacts 425 extend out to the distal end 440 of the circuit board 460. The remaining contacts, two through nine, are off-set from the distal end 440 of the circuit board 460. This arrangement of the ground contacts 425 protruding further than the electrical contacts 424 allows for the hot plugging of the transceiver module 412 to a receptacle assembly which is already operational and powered up. The ground contacts 425 will make electrical contact with the receptacle assembly prior to the electrical contacts 424, allowing the transceiver module to reach the ground potential of the receptacle assembly before the electrical contacts 424 are connected to the receptacle assembly. This arrangement provides a common ground in order to dissipate static discharge to ground potential prior in sequence to connection of other electrical contacts 424. The second side 422 of the circuit board 460 may also have an arrangement similar to the first side 421 of the circuit board 460 in order to provide grounding for hot plugging.

Figure 14:
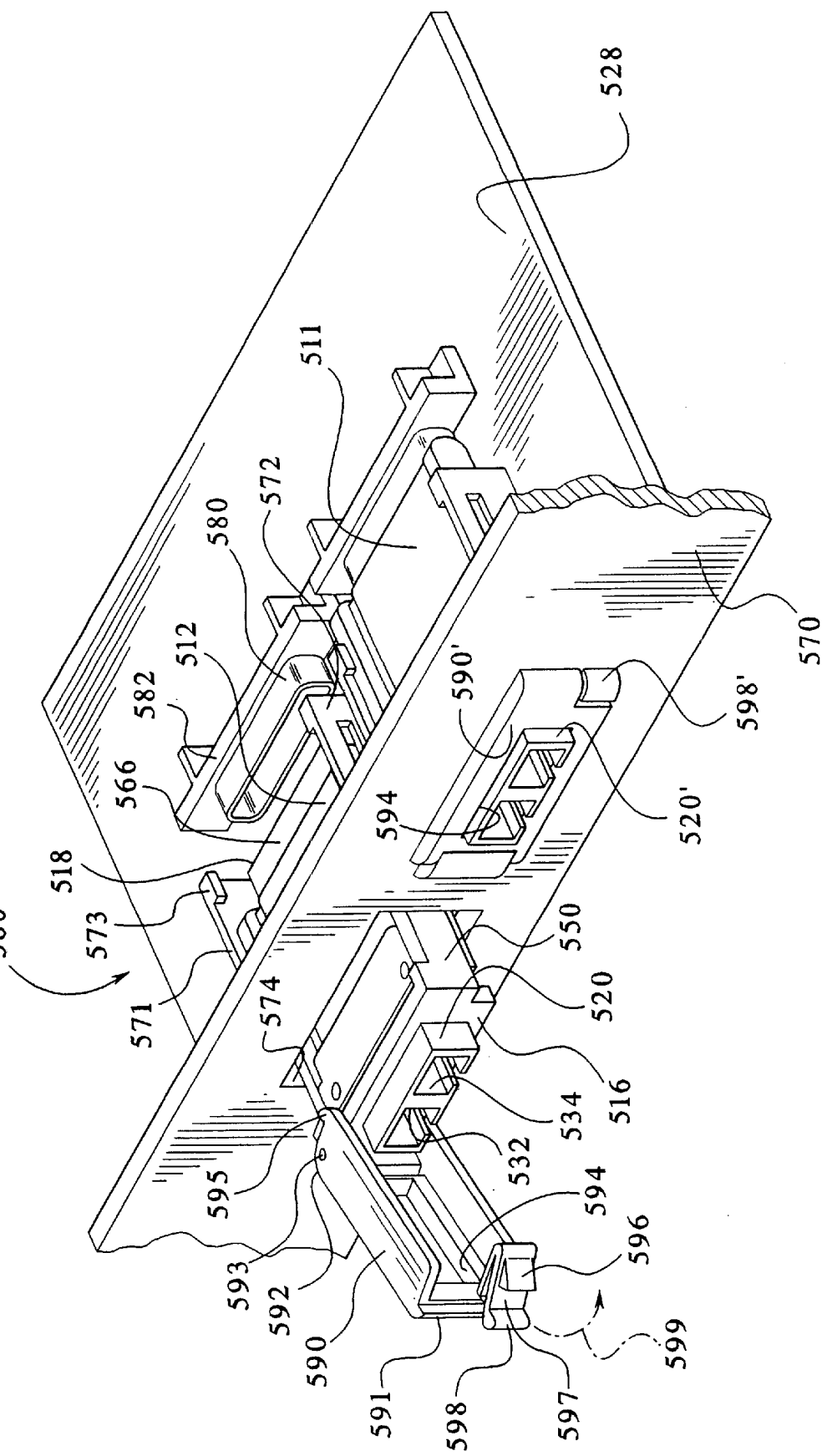
FIG. 14 is a perspective, partially cut-away view of a receptacle of the present invention.

Turning to FIG. 14, a further alternative embodiment of the present invention is shown. In the further alternative embodiment, pluggable transceiver housings 511,512 provide for a pluggable transceiver. However, the pluggable transceiver housings 511,512 have an alternative embodiment to the release levers 350,351 as shown in FIGS. 10 and 11. The transceiver housings 511,512 include a cover latch 590,590' as an alternative means for latching the transceiver housings to a receptacle assembly 500. FIG. 14 shows transceiver housing 512 partially mounted to a receptacle assembly 500. Transceiver housing 511 is shown fully mated to the receptacle assembly 500. The receptacle assembly 500 includes a motherboard or circuit card assembly 528, a mounting panel 570 adjacent and perpendicular to a front side and attached to the motherboard 528, mounting rails 571,572 and a circuit card connector 580 attached to connector bracket 582 which is mounted to the motherboard 528. These elements of the receptacle assembly 500 may also define a housing of a device such as a host computer, server or PC. The elements described relating to the transceiver housing 512 are also included for the transceiver housing 511, but will not be separately identified in order to avoid redundancy.

Transceiver housing 512 includes a first end 516 having a transceiver connector 520 attached thereto. In a preferred embodiment, the transceiver connector 520 receives optical plugs such as a duplex SC fiber optic connector. However, in an alternative embodiment, as discussed above, the transceiver connector 520 may provide an electrical connection by receiving an electrical plug having copper wires. However, in the case where the transceiver connector 520 receives fiber optic plugs, the receptacle openings 532,534 have mounted therein latches for receiving the fiber optic plug and adjacent thereto an optical subassembly mounted within the transceiver housing 512 (see FIG. 2). The transceiver connector 520 is mounted to a transceiver housing frame 550. In a preferred embodiment, the transceiver connector 520 and the transceiver frame 550 are integrally molded of a polymer material. The transceiver frame 550 may also form a potting box as discussed above. Mounted at a second end 518 of the transceiver housing 512 is a pluggable connector 566. In a preferred embodiment, the connector 566 is a D-shaped connector as discussed above (FIG. 13). The pluggable connector 566 being oriented at the second end 518, opposite the first end 516 of the transceiver housing 512, allows for the quick and easy insertion of the transceiver housing 512 into the receptacle assembly 500 and for pluggably mating the transceiver housing 512 to the circuit card connector 580 of the receptacle assembly 500 all in a single motion. The transceiver housing frame 550 is received by guide rails 571,572. The guide rails 571,572 include detentes 573 for guiding the transceiver housing frame 550 and maintaining the transceiver housing 512 in a parallel orientation to the motherboard 528 and for aligning the pluggable connector 566 to the circuit card connector 580.

Upon insertion of the transceiver housing 512 within the receptacle assembly 500, approximately three quarters of the way, the latch cover 590 securely mounts the transceiver housing 512 to the receptacle assembly 500. The latch cover 590 includes a first side 591 and a second side 592. The second side 592 of the latch cover 590 is hingedly attached to the first end 516 of the transceiver housing 512. An attachment means 593 attaches the latch cover 590 so that it swings in a transverse direction to the first end 516 of the transceiver housing 512 in direction of arrow 599. The second side 592 of the latch cover 590 also includes a boss 595. Upon insertion of the transceiver housing 512 into the receptacle assembly 500 and initial rotation of the latch cover in direction of arrow 599, the boss 595 will catch on the mounting panel opening 574. The boss 595 engages the backside of the mounting panel 570 and pushes the transceiver housing 512 toward its completely mated orientation within the receptacle assembly 500. As the latch cover 590 is rotated in direction of arrow 599, it is moved into an orientation so that it is almost parallel with the front surface of the mounting panel so that latch member 596 engages the opening 574 of the mounting panel 570. The latch member 596 is attached to resilient beam 597 attached to the first side 591 of the latch cover 590. Upon engagement of the latch member 596 with the opening 574, the resilient beam 597 is compressed toward the first end 591 of the latch cover 590. The latch cover 590 is then moved to its fully latched position and the resilient beam 592 springs outwardly so that the latch member 596 engages the back of the mounting panel 570. The latch member 596 may be released from its latched position by depressing the release lever 598 attached at the end of the resilient beam 597. In a preferred embodiment, the latch cover 590, latch member 596, resilient beam 597 and release lever 598 are integrally molded of a polymer material.

In an embodiment of the transceiver housing 512, the latch cover 590 may be metallized and the mounting panel 570 also metallized or made of a metallic material and grounded, so that attachment of the transceiver housing 511,512 to the mounting panel 570 via the metallized latch cover 590 automatically grounds the transceiver housings 511,512.

Turning to the transceiver housing 511 shown fully mated with the receptacle assembly 500 in FIG. 14, the latch cover 590' is shown fully latched to the mounting panel 570 so that the front surface of the latch cover 590' is parallel to the front plane of the mounting panel 570. The latch cover 590' includes window 594 from which the transceiver connector 520' protrudes. Upon fully mounting of the transceiver housing 511 within the receptacle assembly 500 and the complete latching of the cover latch 590', plugs may be inserted into the transceiver connector 520'. In many circumstances, the transceiver housing 511 can remain within the receptacle assembly 500 for a long period of time and in some cases, the transceiver housing 511 may never need to be replaced or removed. However, in certain circumstances, the transceiver housing 511 may need updating or repair. The present design allows for the easy removal and reinsertion of the transceiver housing 511. For example, the transceiver housing 511 may need to be modified so that a different media interface transceiver connector 520' may be utilized and added to the housing. Or in another instance, the functioning of the transceiver module may need to be updated by adding a new chip set or optoelectronic subassembly. By depressing the release lever 598' the latch cover 590' may be unlatched and rotated to an "open" position. Once the latch cover 590' is "open," the latch cover 590 may be gripped and used as a handle to aid in pulling the transceiver housing 511 from the receptacle assembly 500. Once removed, the transceiver module housing 511 may then be repaired, replaced or updated.

Figure 15:
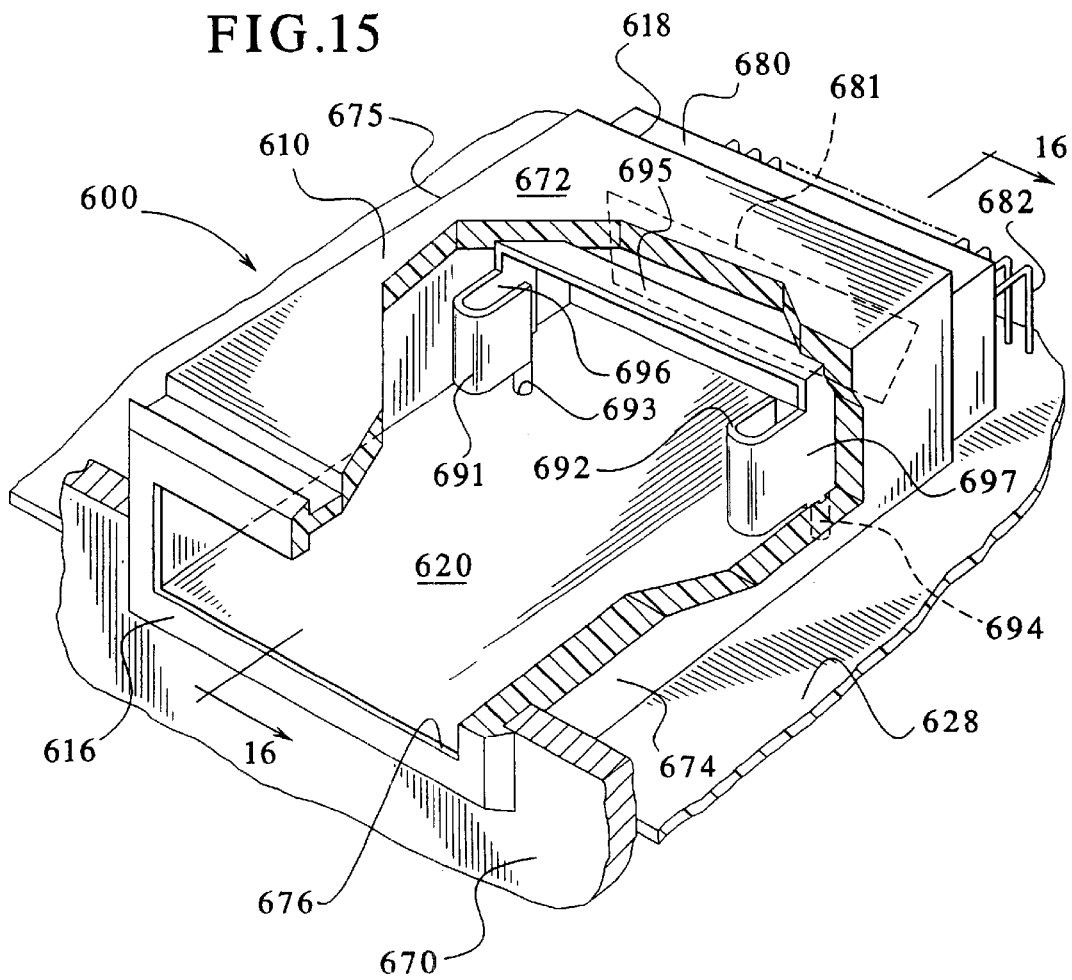
FIG. 15 is a side elevation cut-away view of FIG. 15 taken at line 16—16.
Figure 16:
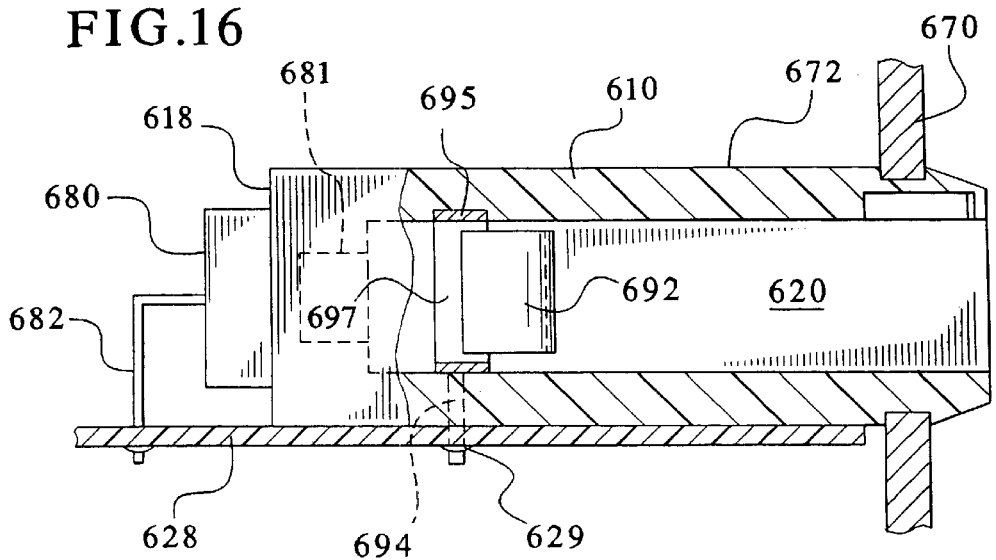
FIG. 16 is a perspective view of an alternative embodiment of a receptacle assembly.

Turning to FIGS. 15–16, a further alternative embodiment of the present invention is shown. Generally, FIGS. 15–16 show a new and improved receptacle for receiving a transceiver module, such as those described herein. For example, the receptacle 310 disclosed in FIG. 10 is more clearly illustrated by reference to FIGS. 15–16. Similarly, the receptacle shown in FIGS. 15–16 is configured to receive the transceiver housing 312 shown in FIGS. 10–11. A receptacle assembly 600 is shown in FIG. 15 having a motherboard 628 and a mounting panel 670 having mounted thereto a transceiver receptacle 610. The receptacle 610 has a first end 616 having an opening 676 and a second end 618 having a connector 680 adjacent thereto. The transceiver receptacle 610 also includes top 672 and sides 674,675.

The walls of the receptacle 610 define a chamber 620. FIG. 15 is partially cut-away to expose the chamber 620 within the receptacle 610. Mounted within the chamber 620 are ground surfaces or tabs 691,692. The ground tabs 691,692 protrude into the chamber 620 and are oriented to abuttingly engage or wipe against the external surfaces of a transceiver module mounted within the receptacle 610. The outer surfaces of a transceiver housing are metallized so that upon insertion within the chamber 620 and engagement with the ground tabs 691,692, the transceiver module will be grounded. The ground tabs 691,692 include ground posts 693,694. The ground posts 693,694 are mounted in and grounded to the motherboard 628. The ground tabs 691,692 are joined by brace 695. The ground tabs 691,692 are attached to the brace 695 via arms 696,697. The arms 696,697 and the brace 695 in a preferred embodiment are insert molded within the receptacle housing 610. The insert molding is controlled so that only the ground tabs 691,692 protrude into the chamber 620 and the ground posts 693,694 protrude out from the bottom of the receptacle 610.

The receptacle connector 680 includes contacts 682 which are attached to the motherboard 628. Protruding into the chamber 620 from the connector 680 is receptacle connector 681 for receiving the D-shaped connector at the end of the transceiver module inserted within the receptacle 610. (See FIG. 10.)

Turning to FIG. 16, a side elevation cut-away view of FIG. 15 taken at line 16—16 is shown. The receptacle housing 610 is shown mounted to the motherboard 628 and the mounting panel 670. Ground clip 692 protrudes into the chamber 620 and grounds the metallized transceiver housing to the motherboard 628. The ground tab 692 is attached to arm 697. Protruding from the arm 697 is ground post 694 which is mounted within the plated through hole of motherboard 628 and is secured to the motherboard with solder 629 and provides for grounding to the motherboard. At least a portion of the arm 697 and a portion of the ground post 694 and brace 695 are molded within the polymer material of the receptacle housing 610. Receptacle connector 680 is attached at the second end 618 of the receptacle 610. Attached to the receptacle connector 680 is D-shaped receptacle 681 and contacts 682.

Figure 17:
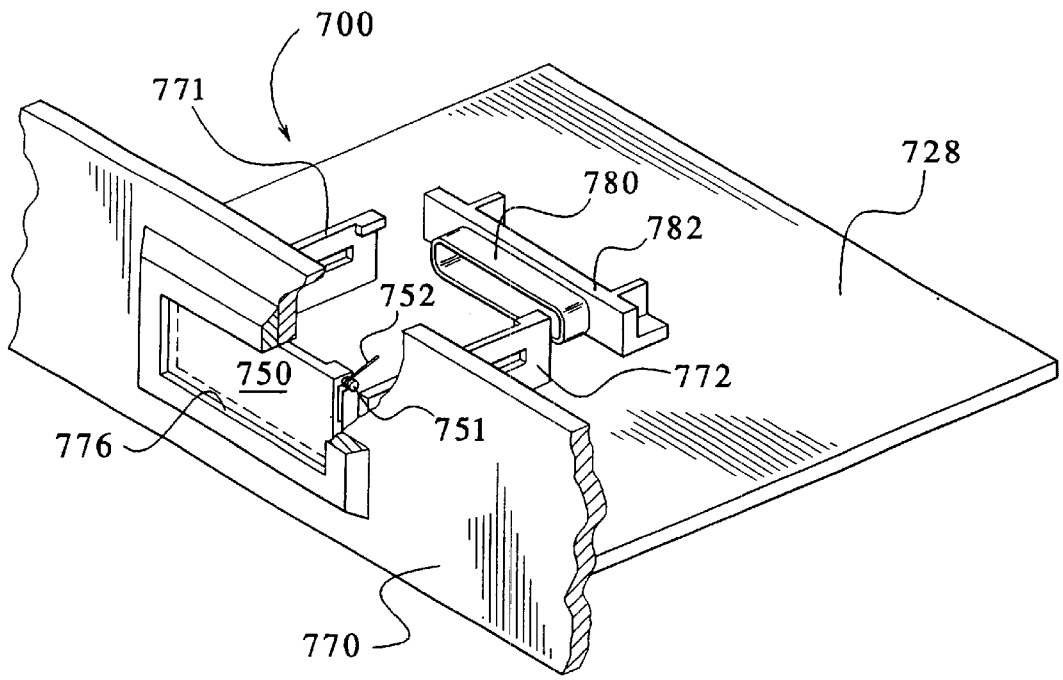
FIG. 17 is a perspective view of another alternative embodiment of a receptacle assembly of the present invention.

Turning to FIG. 17 an alternative embodiment is provided where the receptacle assembly 700 includes a circuit card assembly or mother board 728, a mounting panel 770, mounting rails 771, 772 and a circuit card connector 780 attached to connector bracket 782. Mounted to the mounting panel 770 is a protective door 750. The mounting panel 770 is partially broken away to more clearly show the door 750. The door 750 is hinged at a point at the top of the door 750. Post 751 protrudes from the edge of the door and is received by an aperture in the mounting panel 770. Mounted on the post 751 is a resilient member 752 such as a spring. The spring 752 is configured in order to return the door 750 to its closed position parallel to the front face of the mounting panel 770 after the door 750 has been opened. The protective door 750 acts as a shield in order to limit electromagnetic radiation from escaping from the receptacle assembly 700 when the receptacle assembly 700 is empty. Certain power sources and components mounted to the motherboard 728 may develop electromagnetic emissions. In absence of a door such as 750 upon removal of a transceiver module from the receptacle assembly 700, the electromagnetic emissions generated by the components mounted on the motherboard 728 would be free to escape through the opening 776. Attachment of the protective door 750 to the mounting panel inhibits these emissions. The protective door 750 may be metal or metallized in order to further reduce such emissions. Also by incorporation of door 750 to the receptacle assembly 700 the receptacle may be left empty upon initial construction of the receptacle assembly 700, allowing for assembly of multiple receptacle assemblies 700 on motherboard 728 for reception of additional transceiver modules at a later date. The post 751 provides for a hinge to the door 750 and allows for the swinging motion of the door. The door 750 is hinged so that upon abutment of a transceiver module against the door and attempted insertion of the transceiver module through opening 776, the door will swing inwardly allowing the transceiver module to be inserted therein. While the transceiver module is housed within the receptacle assembly 700 the door 750 will remain in an upright position adjacent the top of the transceiver module. Upon removal of the transceiver module from the receptacle assembly 700, the spring 752 causes the door 750 to swing back to its closed position parallel to the front face of the mounting panel 770.

Figure 18:
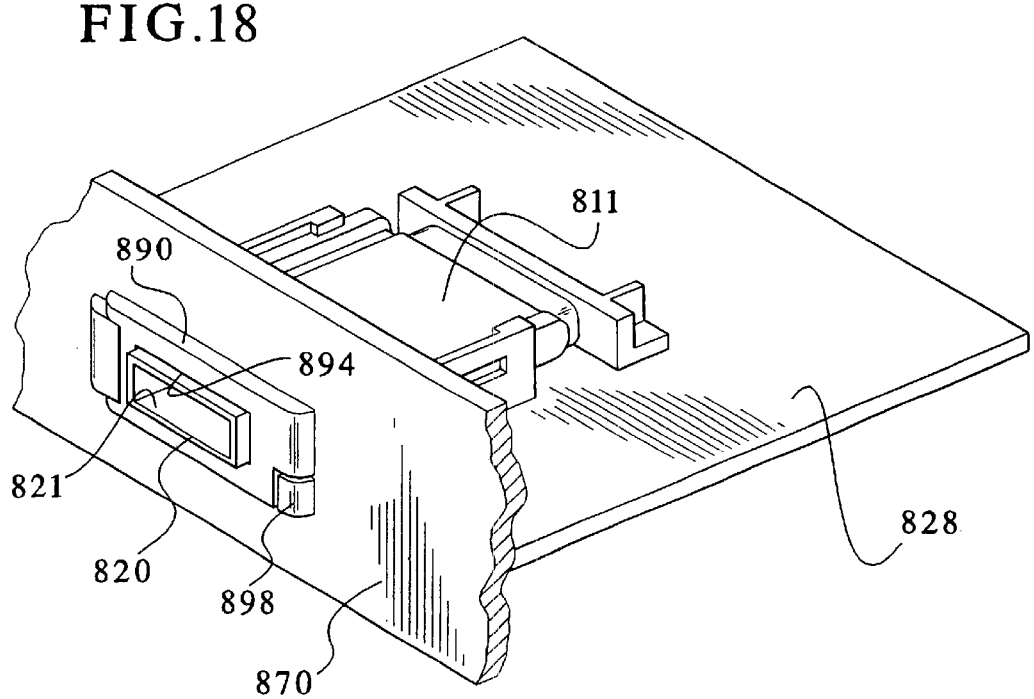
FIG. 18 is a perspective view of an alternative embodiment of the present invention shown in an unmated orientation.

Turning to FIG. 18, another alternative embodiment of the present invention is shown. Attached to the transceiver housing 811 is a transceiver connector 820 which is an alternative embodiment of the transceiver connector 520 of transceiver housing 512 of FIG. 14. The transceiver connector 820 is shown having a modular port 821. The modular port 821 is configured so that any number of receptacle connectors may be inserted therein for receiving various types of plugs. Due to the easily removable nature of the transceiver module 811, the transceiver can be removed so that a plug receptacle (not shown) mounted within the modular port 821 may be removed and disconnected from the components within the transceiver module 811 and a new plug receptacle inserted within the modular port 821 and connected to the components of the transceiver module 811. Such an operation is best accomplished by the manufacturer using this orientation to achieve quick assembly and just-in-time manufacture and to avoid remolding of the entire module housing. The transceiver module 811 can then be easily reinserted and attached to the receptacle assembly 800. For example, the transceiver module 811 may be configured for transmitting and receiving electrical signals from an external device having an electrical plug inserted into the transceiver connector 820, as discussed above. Such a copper plug would be inserted into a copper plug receptacle which is mounted within the modular port 821. For example, a DB-9 connector may be used. In another embodiment, an alternative fiber optic receptacle could be inserted within the modular port 821. For example, a multiple channel connector such as an MT connector could be attached to the transceiver housing 811 by inserting an updated optical fiber receptacle within the modular port 821 of the transceiver connector 820 to receive a multi-channel connector.

In another embodiment, a media transducer may be inserted within modular port 821. The media transducer may include at a first end a connector receptacle such as coaxial connector 420 of FIG. 12 or an SC duplex connector 520 of FIG. 12. A second end of the media transducer may include an optoelectronic subassembly such as a PIN diode, laser diode such as LED and other optical circuitry for optical media; or an electrical subassembly such as a transformer or other AC coupling means for copper media. In another embodiment, the media transducer may include only a connector receptacle or only an optoelectronic or electronic subassembly. Such a media transducer would allow for the updating or changing of the media interface by removing the media transducer from the modular port 820 and replacing with another media transducer. It should be understood that in describing the top and bottom portions of the transceiver module and its respective potting box components, the terms "top" and "bottom" are used by way of example only due to the orientation of the drawings. It should also be understood that various changes and modifications to the presently preferred embodiments described herein will be apparent to those skilled in the art. Furthermore, although the transceiver module depicted in the presently preferred embodiment has its male ribbon style connector extending from the bottom, it should be understood from the outset that the connector can be configured to extend, for example, from the second end of the transceiver. Therefore, changes and modifications may be made without departing from the spirit and scope of the present invention and without diminishing its attendant advantages. Thus, it is intended that such changes and modifications be covered by the appended claims.

We claim:

1. A transceiver module and receptacle assembly comprising:
   a transceiver module housing having a first end and a second end;
   a circuit board mounted within the housing and an optical subassembly electrically connected to the circuit board;
   a pluggable male ribbon style electrical connector at the second end connected to said circuit board and protruding from said housing for quickly installing and replacing said module to or from a circuit card assembly and the male ribbon style connector having at least a pair of metallic fingers extending from said housing on opposed sides of an insulator;

a conductive portion of the housing to provide for electromagnetic shielding; and a grounding means associated with the receptacle and providing an electrical connection between the receptacle and the conductive portion of the housing in order to ground the module and enhance the electromagnetic shielding.

2. The transceiver module and receptacle assembly of claim 1 including a latching means having release levers attached to the sides of the transceiver module housing and latching to the interior surface of the receptacle.

3. The transceiver module and receptacle assembly of claim 1 including:

a receptacle housing defining a chamber; and the grounding means of the receptacle includes a ground surface protruding within the chamber.

4. The transceiver module and receptacle assembly of claim 3 wherein the ground surface is attached to an arm, which is molded within the receptacle housing.

5. The transceiver module and receptacle assembly of claim 1 including:

a receptacle housing having a first end having a protective door mounted thereto.

6. The module and receptacle assembly of claim 5 wherein the door frictionally engages the first end of the receptacle and may be easily moved from a first position blocking the first end to a second position opening the first end.

7. The transceiver module and receptacle assembly of claim 1 including:

the transceiver module housing wherein the conductive portion comes into contact with the grounding means of the transceiver receptacle via a direct electrical and mechanical contact in order to provide grounding of the transceiver module to the receptacle.

8. The transceiver module and receptacle assembly of claim 7 wherein the transceiver module conductive portion is metallized and upon insertion within the receptacle, the metallized transceiver module housing abuts against a ground surface protruding within the receptacle chamber in order to ground the transceiver module to the receptacle.

9. The transceiver module and receptacle assembly of claim 1 including a transceiver connector attached to the first end of the transceiver module housing.

10. The transceiver module and receptacle assembly of claim 9 wherein the transceiver connector is a fiber optic plug receptacle integrally formed with the housing of the transceiver module.

11. The transceiver module and receptacle assembly of claim 10 wherein the transceiver module the end wall having a through port.

12. The transceiver module and receptacle of claim 11 wherein the optical subassembly is adjacent the through port.

13. The transceiver module of claim 12 wherein the through port allows light to pass from the optical subassembly out of the transceiver module.

14. A transceiver module comprising:

a transceiver module housing having a first end and a second end;

a circuit board mounted within the housing and a transmitting subassembly electrically connected to the circuit board;

a release lever mounted to the transceiver module housing adjacent the first end and a pluggable male ribbon style electrical connector at the second end connected to said circuit board and protruding from said housing for quickly installing and replacing said module to or from a circuit card assembly;

the housing including an external conductive surface shielding a portion of the module; and a ground member electrically connected to the conductive surface in order to reduce electromagnetic interference and provide for an FCC compliant module.

15. The transceiver module of claim 14 wherein the transceiver module includes an optoelectronic subassembly.

16. The transceiver module of claim 14 wherein a pair of release levers are attached at a first end of a module.

17. The transceiver module and receptacle assembly of claim 14 wherein the ground member includes a ground clip attached at the first end of the module.

18. The transceiver module of claim 17 wherein the ground clip is formed with the housing.

19. An optoelectronic module comprising:

a housing including a first end wall;

a circuit board mounted within said housing and an optical subassembly connected to said circuit board;

a male ribbon style electrical connector at a second end of said housing connected to said circuit board and protruding from said housing for quickly installing and replacing said module to or from a circuit card assembly and the male ribbon style connector having at least a pair of metallic fingers extending from said housing to provide for hot plugging of the module; and a ground tab providing an electrical connection between the housing of the module and a chassis faceplate of a host device to which the module is mounted.

20. The optoelectronic module of claim 19 wherein the electrical connector protrudes perpendicularly from an end face of the second end and parallel to the circuit board.

21. The optoelectronic module of claim 19 wherein the pair of metallic fingers extend from said housing on opposed sides of an insulator and a ground contact is offset and extends beyond a signal contact.

22. The optoelectronic module of claim 19 wherein said housing includes a release member for facilitating the insertion and removal of said module to and from a circuit card assembly.

23. The optoelectronic module of claim 19 wherein the release member is mounted to the housing adjacent the first end.

24. The optoelectronic module of claim 19 wherein the ground tab protrudes from the housing of the module and will make contact with a chassis faceplate of the host device.

25. The optoelectronic module of claim 24 wherein the ground tab provides for static discharge.

26. The optoelectronic module of claim 24 wherein the ground tab establishes a reference voltage.

27. A transceiver module comprising:

a module including a first end, a second end, a circuit board, and a transmitting subassembly electrically connected to the circuit board;

a release lever mounted to the module adjacent the first end;

said module including an external conductive surface shielding a portion of the module; and a ground member electrically connected to the conductive surface in order to reduce electromagnetic interference and provide for an FCC compliant module.

28. The transceiver module of claim 27, wherein the transceiver module includes an optoelectronic subassembly.

29. The transceiver module of claim 27, wherein a pair of release levers are attached proximate the first end of the module.

30. The transceiver module of claim 27, wherein the ground member includes a ground clip attached at the first end of the module.

31. The transceiver module of claim 30, wherein a portion of the ground clip is formed with the module.

32. An optoelectronic module comprising:

a module including a first end wall;

an optical subassembly connected to a circuit board and;

a male ribbon style electrical connector at a second end of said module connected to said circuit board for quickly installing and replacing said module to and from a circuit card assembly, and the male ribbon style connector having at least a pair of metallic fingers extending from said module to provide for hot plugging of the module; and a ground tab providing an electrical connection between the module and a chassis faceplate of a host device to which the module is mounted.

33. The optoelectronic module of claim 32, wherein the electrical connector protrudes perpendicularly from an end face of the second end and parallel to the circuit board.

34. The optoelectronic module of claim 32, wherein the pair of metallic fingers extend from said module on opposing sides of an insulator and a ground contact is offset and extends beyond a signal contact.

35. The optoelectronic module of claim 32, wherein said module includes a release member for facilitating the insertion and removal of said module to and from a circuit card assembly.

36. The optoelectronic module of claim 32, wherein the release member is mounted to the housing adjacent the first end.

37. The optoelectronic module of claim 32, further comprising potting material inside the module.

38. The optoelectronic module of claim 32, wherein the module is hermetically sealed.

39. The optoelectronic module of claim 32, wherein the ground tab protrudes from the module and makes contact with a chassis faceplate.

40. The optoelectronic module of claim 39, wherein the ground tab provides for static discharge.

41. The optoelectronic module of claim 39, wherein the ground tab establishes a reference voltage.

* * * * *